(12) United States Patent
Adair et al.

(10) Patent No.: US 7,002,621 B2
(45) Date of Patent: Feb. 21, 2006

(54) COMMUNICATION DEVICES INCORPORATING REDUCED AREA IMAGING DEVICES

(76) Inventors: Edwin L. Adair, 317 Paragon Way, Castle Pines Village, CO (US) 80104; Jeffrey L. Adair, 1861 E. Redfox Pl., Highlands Ranch, CO (US) 80126; Randall S. Adair, 3082 S. Flamingo Way, Denver, CO (US) 80222

(*) Notice: Subject to any disclaimer, the term of this patent is extended or adjusted under 35 U.S.C. 154(b) by 759 days.

(21) Appl. No.: 09/934,201

(22) Filed: Aug. 21, 2001

(65) Prior Publication Data

US 2002/0089589 A1   Jul. 11, 2002

Related U.S. Application Data

(63) Continuation-in-part of application No. 09/613,027, filed on Jul. 10, 2000, which is a continuation-in-part of application No. 09/496,312, filed on Feb. 1, 2000, now Pat. No. 6,275,255, which is a continuation of application No. 09/175,685, filed on Oct. 20, 1998, now Pat. No. 6,043,839, which is a continuation-in-part of application No. 08/944,322, filed on Oct. 6, 1997, now Pat. No. 5,929,901.

(51) Int. Cl.
*H04Q 7/32* (2006.01)

(52) U.S. Cl. .................................... 348/158; 455/556

(58) Field of Classification Search ............ 348/65–76, 348/155–159, 373–376, 60–400; 455/556–566, 455/400–600

See application file for complete search history.

(56) References Cited

U.S. PATENT DOCUMENTS

| 4,491,865 A | 1/1985 | Danna et al. ................. 358/98 |
| 4,745,471 A | 5/1988 | Takamura et al. ............ 358/98 |
| 4,786,965 A | 11/1988 | Yabe ........................... 358/98 |

(Continued)

FOREIGN PATENT DOCUMENTS

DE   199 47 875   4/2001

(Continued)

OTHER PUBLICATIONS

Hsieh et al.; "Low-Power parallel Video Compression Architecture for a Single-Chip Digital CMOS Camera"; *Journal of VLSI Signal Processing*; vol. 21, 1999; pps. 195-207.

(Continued)

*Primary Examiner*—Andy Rao
(74) *Attorney, Agent, or Firm*—Sheridan Ross PC

(57) ABSTRACT

A reduced area imaging device is provided for use with a communication device, such as a wireless/cellular phone. Various configurations of the imaging device are provided which locate the elements of the imaging device at desired locations. The communication device includes a miniature LCD-type monitor which displays not only images taken by the camera module, but also incoming video messages. The camera module may communicate with the housing of the communication device by wired connection, or wirelessly. The camera module is of such small size that it can be stored within the housing of the communication device. The camera module may be pointed at any object within sight of the user, without having to move the phone housing in order to take video images. Any acceptable wireless standard may be used for wireless communication between the camera module and the video telephone. One particularly advantageous wireless standard includes Bluetooth.

62 Claims, 14 Drawing Sheets

U.S. PATENT DOCUMENTS

| | | | |
|---|---|---|---|
| 4,814,648 A | 3/1989 | Hynecek | 307/497 |
| 4,854,302 A | 8/1989 | Allred, III | 128/6 |
| 4,869,246 A | 9/1989 | Adair | 128/303.1 |
| 4,928,300 A | 5/1990 | Ogawa et al. | |
| 4,942,473 A | 7/1990 | Zeevi et al. | 358/213.26 |
| RE33,854 E | 3/1992 | Adair | 128/6 |
| 5,116,317 A | 5/1992 | Carson, Jr. et al. | 604/96 |
| 5,162,913 A | 11/1992 | Chatenever et al. | 358/213.19 |
| 5,220,198 A | 6/1993 | Tsuji | 257/731 |
| 5,251,613 A | 10/1993 | Adair | 128/6 |
| 5,381,784 A | 1/1995 | Adair | 128/6 |
| 5,402,768 A | 4/1995 | Adair | 128/4 |
| 5,453,785 A | 9/1995 | Lenhardt et al. | 348/357 |
| 5,471,515 A | 11/1995 | Fossum et al. | 377/60 |
| 5,489,256 A | 2/1996 | Adair | 600/133 |
| 5,605,531 A | 2/1997 | Lane et al. | 600/118 |
| 5,612,732 A | 3/1997 | Yuyama et al. | |
| 5,630,782 A | 5/1997 | Adair | 600/133 |
| 5,630,783 A | 5/1997 | Steinberg | 600/158 |
| 5,682,199 A | 10/1997 | Lankford | 348/72 |
| 5,701,155 A | 12/1997 | Wood et al. | 348/72 |
| 5,711,013 A | 1/1998 | Collet et al. | |
| 5,734,418 A | 3/1998 | Danna | 348/76 |
| 5,748,411 A | 5/1998 | Hwang | |
| 5,754,313 A | 5/1998 | Pelchy et al. | 358/473 |
| 5,801,919 A | 9/1998 | Griencewic | |
| 5,900,875 A | 5/1999 | Haitani et al. | |
| 5,929,901 A | 7/1999 | Adair et al. | |
| 5,980,450 A | 11/1999 | Thompson | 600/112 |
| 5,983,073 A | 11/1999 | Ditzik | |
| 6,009,336 A | 12/1999 | Harris et al. | |
| 6,018,670 A | 1/2000 | Degenhardt | |
| 6,023,241 A * | 2/2000 | Clapper | 324/357.13 |
| 6,028,764 A | 2/2000 | Richardson et al. | 361/681 |
| 6,067,313 A | 5/2000 | Cafarella et al. | |
| 6,073,034 A * | 6/2000 | Jacobsen et al. | 455/566 |
| 6,083,353 A | 7/2000 | Alexander | |
| 6,104,334 A | 8/2000 | Allport | |
| 6,141,037 A * | 10/2000 | Upton et al. | 348/65 |
| 6,147,366 A * | 11/2000 | Drottar et al. | 257/82 |
| 6,154,254 A * | 11/2000 | Hawkins et al. | 348/374 |
| 6,177,950 B1 | 1/2001 | Robb | |
| 6,184,804 B1 | 2/2001 | Harrison | |
| 6,370,282 B1 | 4/2002 | Pavely et al. | |
| 6,413,209 B1 | 7/2002 | Thompson | 600/169 |
| 6,417,882 B1 | 7/2002 | Manhat-Shetti | |
| 6,452,626 B1 | 9/2002 | Adair et al. | |
| 6,561,669 B1 | 5/2003 | Naghi et al. | |
| 6,658,272 B1 | 12/2003 | Lenchik et al. | |
| 6,730,900 B1 | 5/2004 | Hsish et al. | |
| 6,862,036 B1 | 3/2005 | Adair et al. | |

FOREIGN PATENT DOCUMENTS

| | | |
|---|---|---|
| EP | 0 492 349 A1 | 1/1992 |
| EP | 0 932 302 | 7/1999 |
| WO | WO 97/26744 | 7/1997 |
| WO | WO 98/19435 | 5/1998 |

OTHER PUBLICATIONS

Tariq et al.; "Robust and Scalable Matching Pursuits Video Transmission Using the Bluetooth Air Interface Standard"; *IEEE Transactions on Consumer Electronics;* vol. 46(3); 2000; pps. 673-81.

Nixon et al.; "Active-Pixel Image Sensor Integrated with Readout Circuits"; *NASA Tech Briefs,* Oct. 1996, pps. 38, 40.

Zamowski et al.; "Imaging options expand with CMOS technology"; *Laser Focus World,* Jun. 1997, 5 pages.

Meyerson; "Kids, I'm dialing Grandma now, so stand straight . . . and smile!"; *Denver Rocky Mountain News,* Sep. 5, 2000, pp. 12B.

Drexler; "See and say: Wireless video phone on the way"; Publication date unknown; 4 pages; http://www.cnn.com/TECH/computing/9909/27/nec.vid.phone.idg.

"Wireless Pictures—Part of a New Technology"; Publication date unknown; 4 pages; http://www.kodak.com/US/en/corp/researchDevelopment/technologyFeatures/wireless.shtml.

"Sanyo Semiconductor Adds Bluetooth Connectivity To Digital Camera Chips With Tality Intellectual Property"; Sanyo Press Release San Jose, CA—Dec. 5, 2000; 2 pages; http://www.tality.com//news_events/release/pr-bluetooth_sanyo.html.

"Ericsson Unveils the T68, A GPRS Phone With MMS, A Color Display And Bluetooth"; Press Release Stockholm, Sweden—(Business Wire)-Mar. 21, 2001; 2 pages. http://biz.yahoo.com/bw/010321/2239.html.

"Nokia and Fujifilm to cooperate in developing Bluetooth technology to send digital still images and applications technology"; Press Release Nokia and Fuji Photo Film Co., Ltd. of Japan-(Feb. 14, 2000); 1 page; http://press.nokia.com/PR/200002/775373_5.html.

"Active-Pixel Image Sensor Integrated with Readout Circuits"; NASA Tech Briefs, Oct. 1996.

"Applications Hold the Key to Imager Choice"; Photonics Spectra, Mar. 1997.

"CMOS Image Sensors Challenge CCDs", Microdesign Resources, Jun. 22, 1998, Microprocessor Report, pp. 1-5.

"Imaging Options Expand with CMOS Technology"; Laser Focus World, Jun. 1997.

"NASA's Tiny Camera Has a Wide-Angle Future"; Business Week, Mar. 6, 1995.

"Silicon Eyes", Business Week, pp. 94-100, Oct. 12, 1998.

Hsieh et al.; "Low-Power parallel Video Compression Architecture for a Single-Chip Digital CMOS Camera"; Journal of VLSI Signal Processing; vol. 21, 1999; pps. 195-207.

Tariq et al.; "Robust and Scalable Matching Pursuits Video Transmission Using the Bluetooth Air Interface Standard"; IEEE Transactions on Consumer Electronics; vol. 46(3); 2000; pps. 673-81.

* cited by examiner

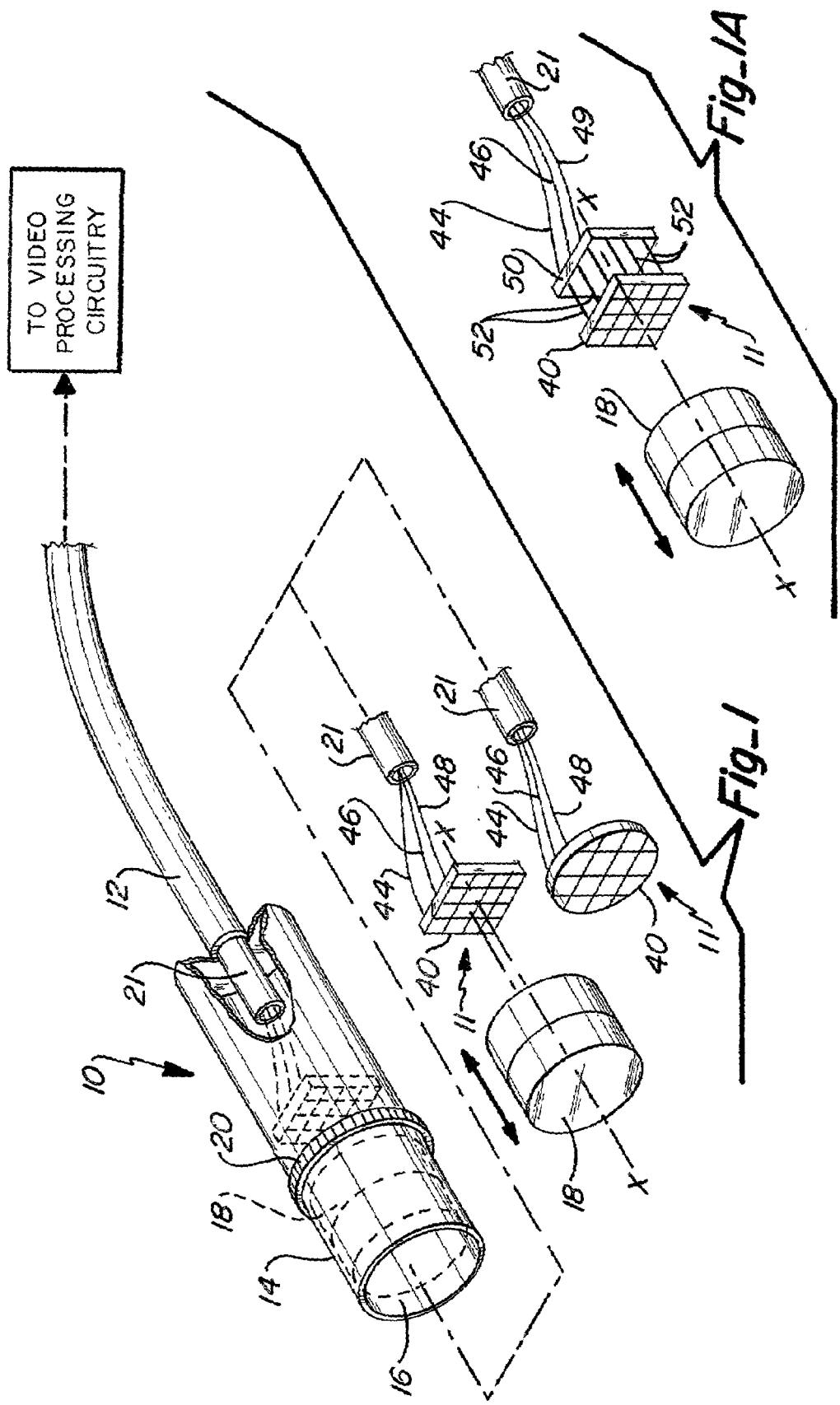

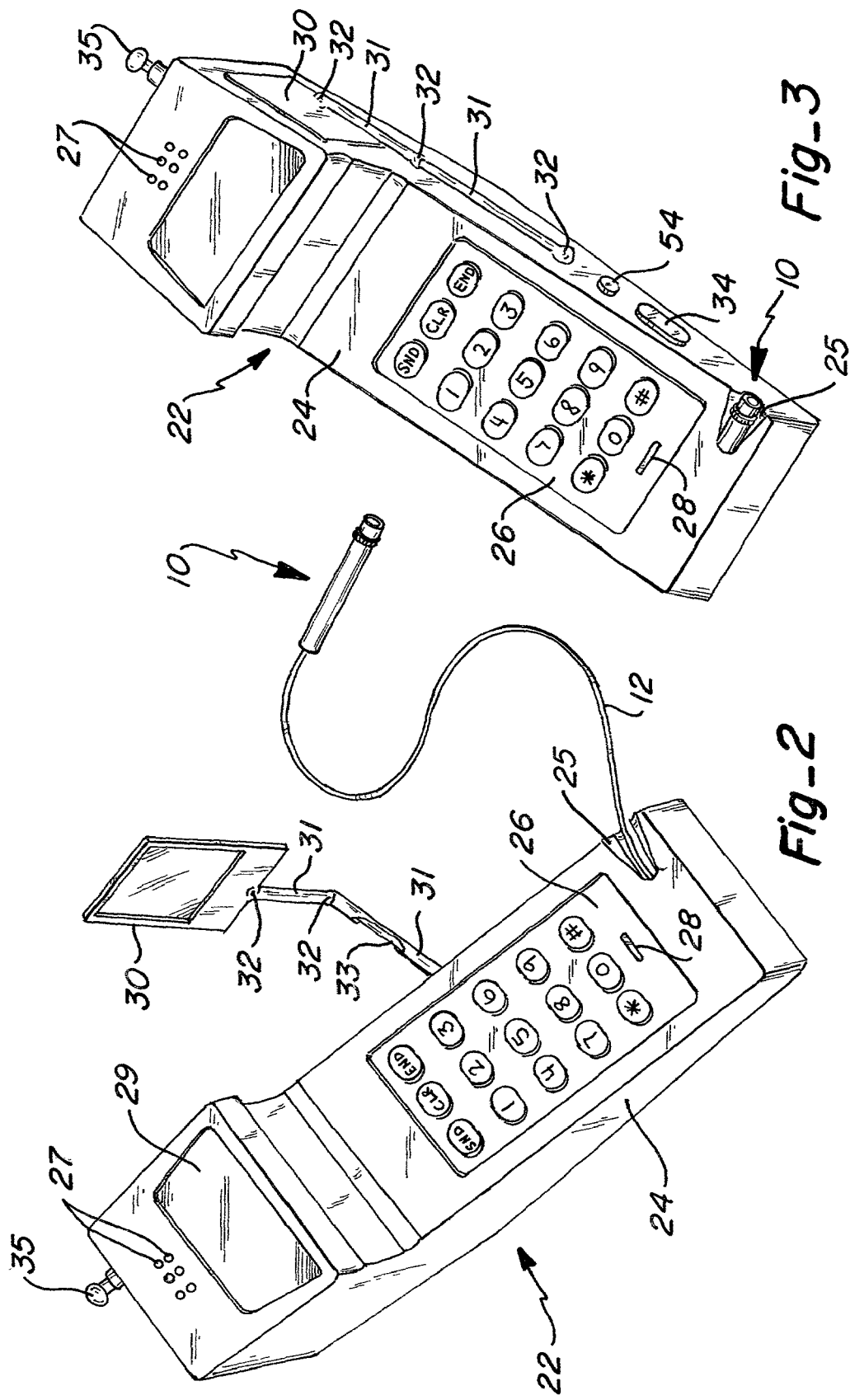

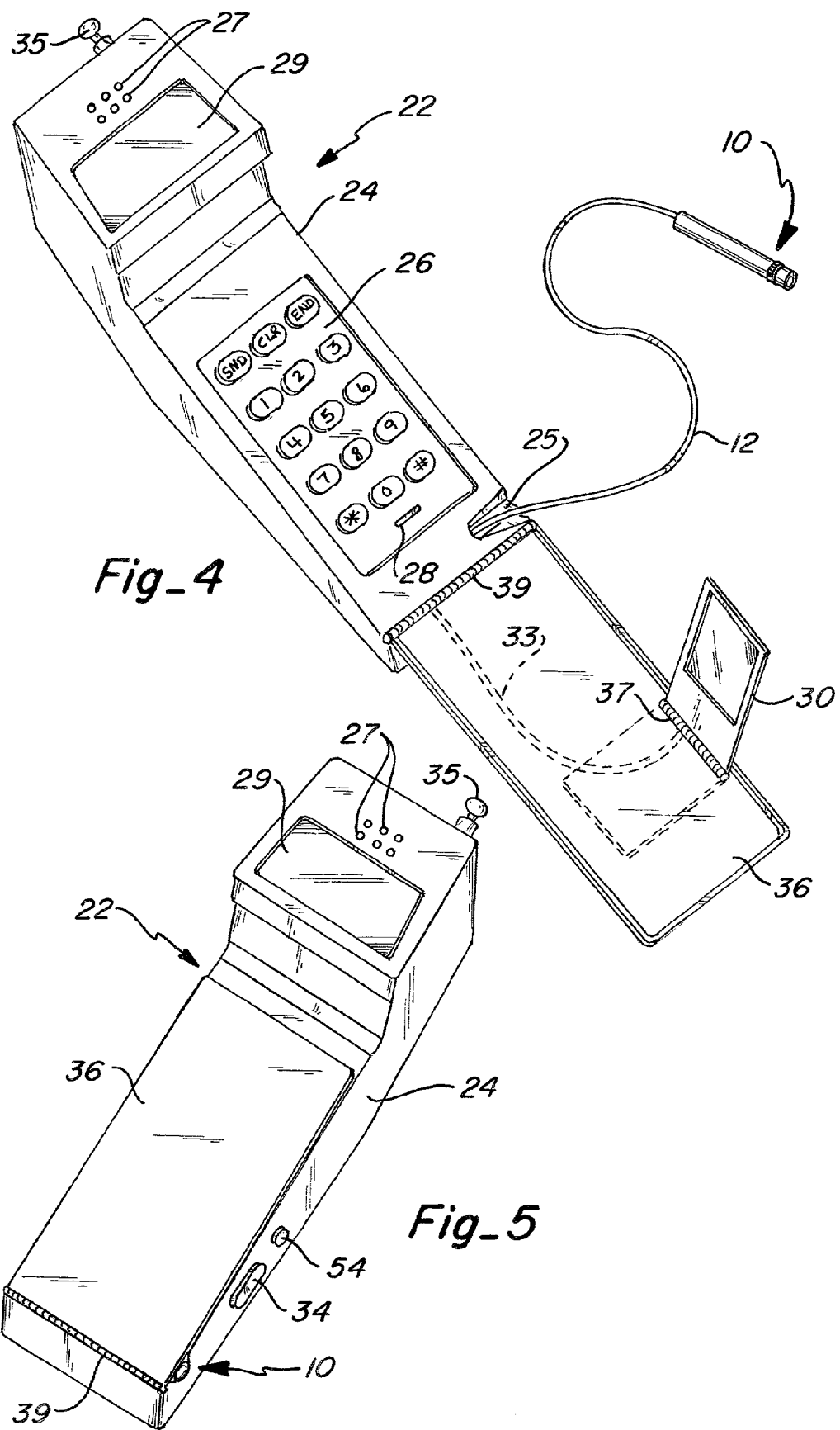

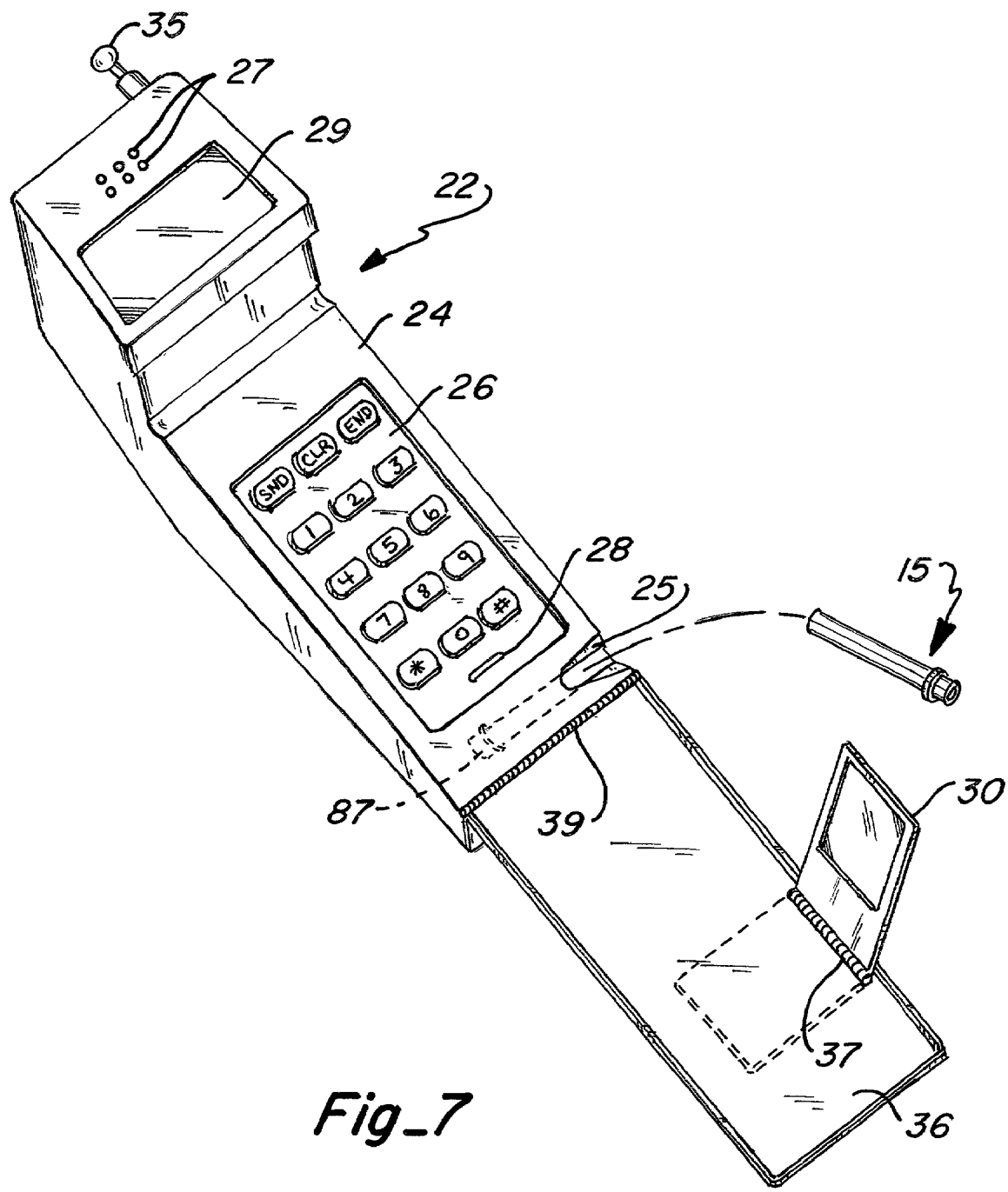
Fig_7

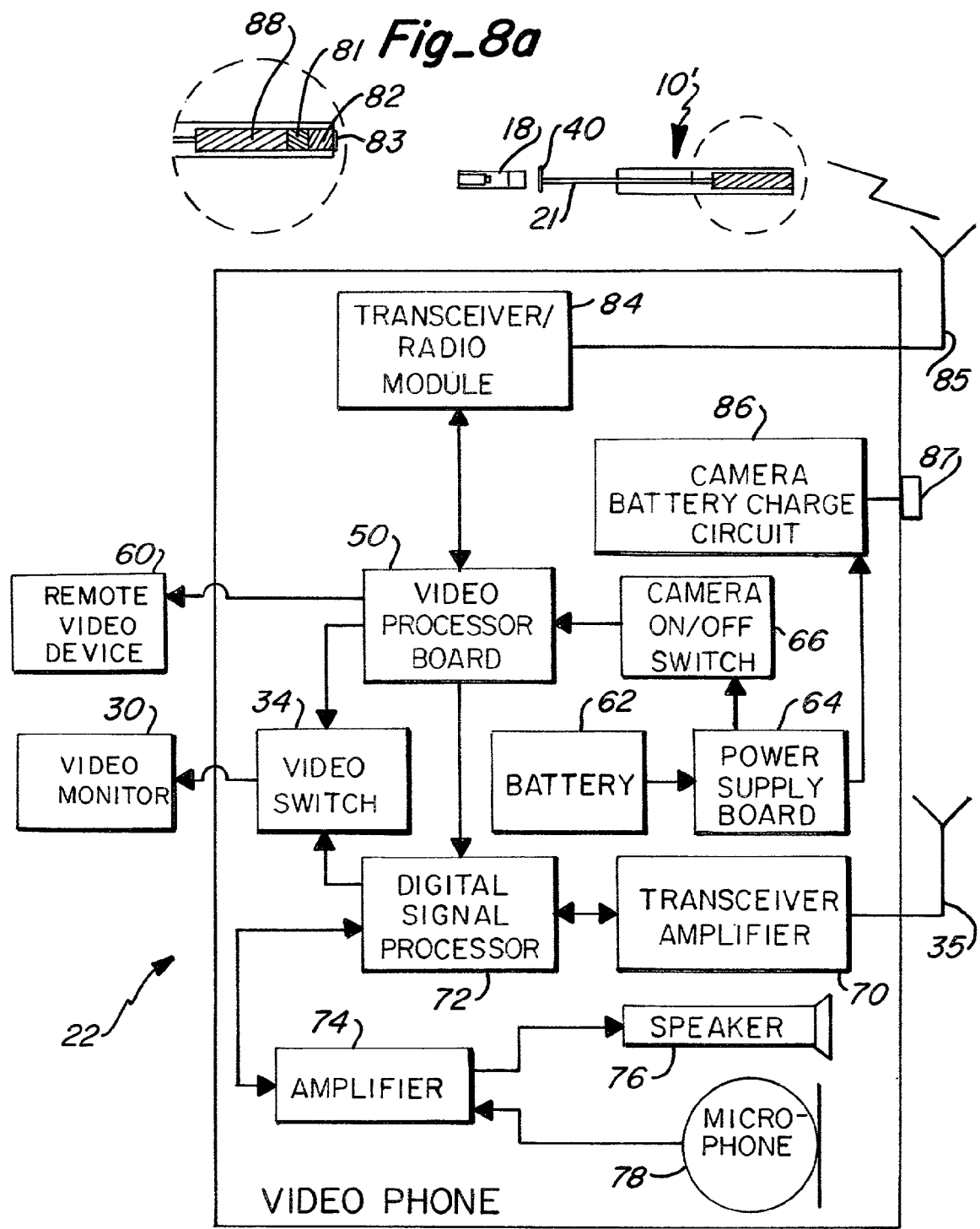

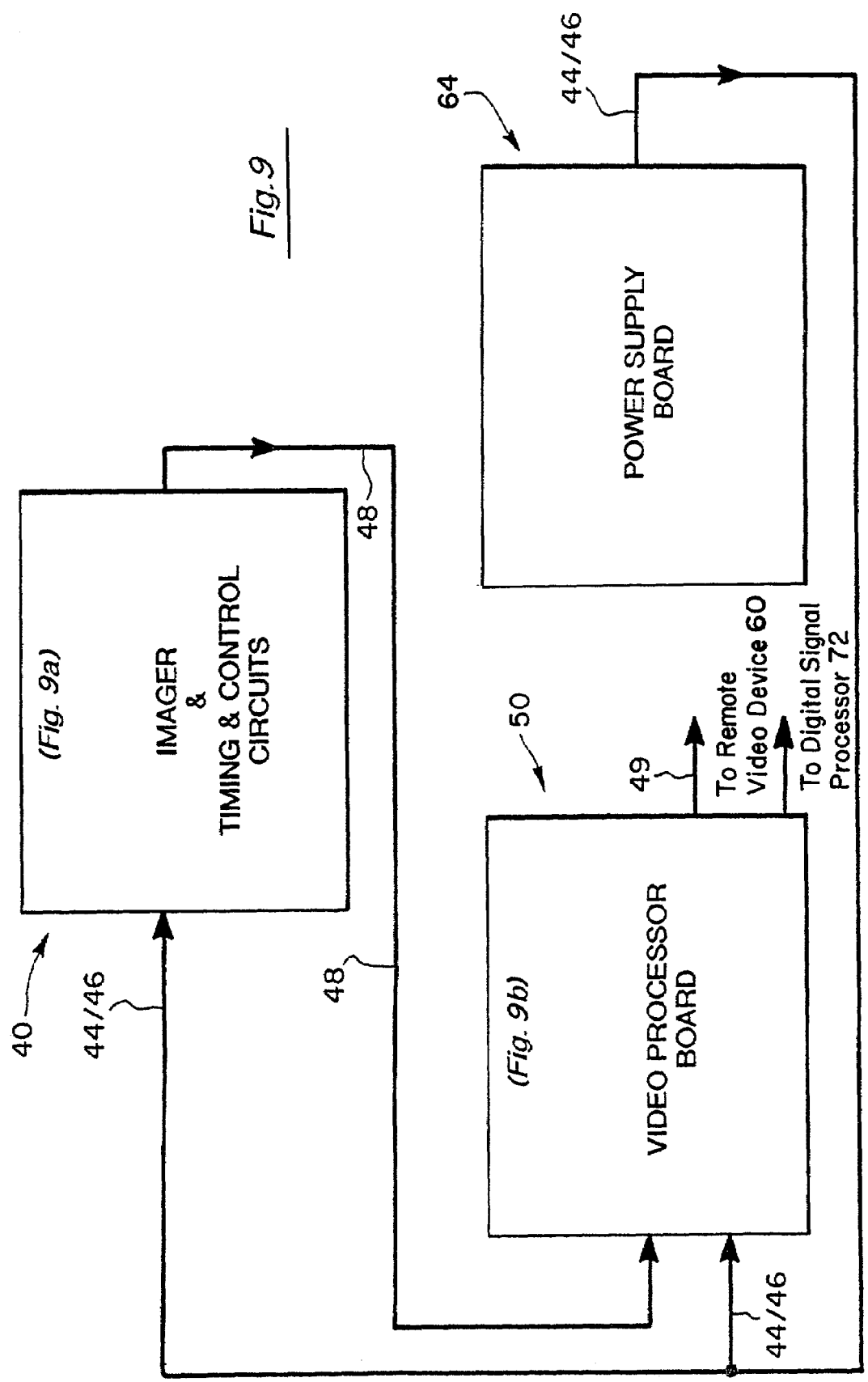

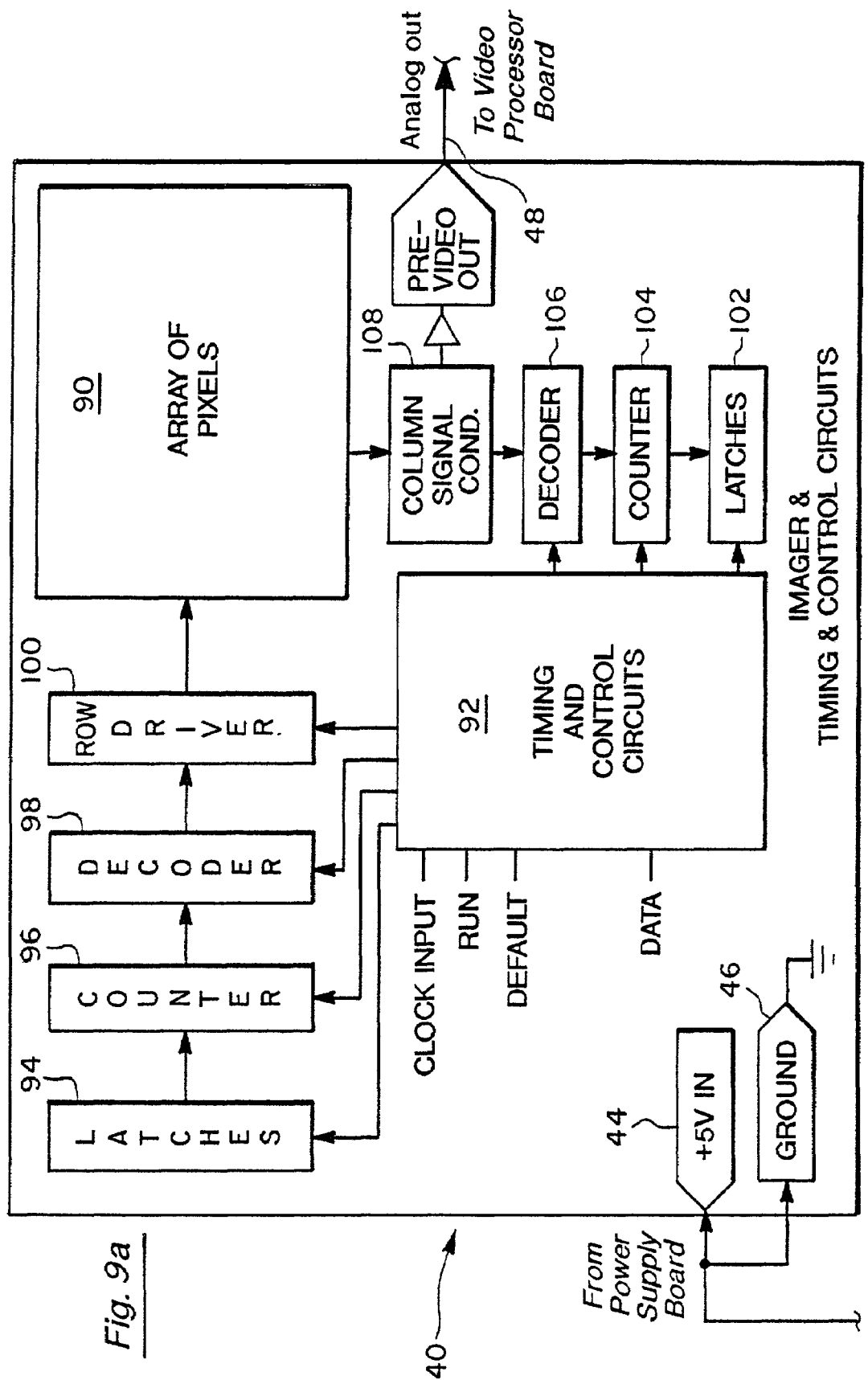

COMMUNICATION DEVICES INCORPORATING REDUCED AREA IMAGING DEVICES

This application is a continuation-in-part of U.S. patent application Ser. No. 09/613,027 filed on Jul. 10, 2000 entitled "Communication Devices Incorporating Reduced Area Imaging Devices", which is a continuation in part of U.S. Ser. No. 09/496,312, filed Feb. 1, 2000 now U.S. Pat. No. 6,275,255, and entitled "Reduced Area Imaging Devices", which is a continuation application of U.S. Ser. No. 09/175,685, filed Oct. 20, 1998 and entitled "Reduced Area Imaging Devices", now U.S. Pat. No. 6,043,839, which is a continuation-in-part of U.S. Ser. No. 08/944,322, filed Oct. 6, 1997 and entitled "Reduced Area Imaging Devices Incorporated Within Surgical Instruments", now U.S. Pat. No. 5,929,901.

TECHNICAL FIELD

This invention relates to solid state image sensors and associated electronics, and more particularly, to solid state image sensors which are configured to be of a minimum size and used within communication devices specifically including video telephones.

BACKGROUND ART

The three most common solid state image sensors include charged coupled devices (CCD), charge injection devices (CID) and photo diode arrays (PDA). In the mid-1980s, complementary metal oxide semiconductors (CMOS) were developed for industrial use. CMOS imaging devices offer improved functionality and simplified system interfacing. Furthermore, many CMOS imagers can be manufactured at a fraction of the cost of other solid state imaging technologies.

The CCD device is still the preferred type of imager used in scientific applications. Only recently have CMOS-type devices been improved such that the quality of imaging compares to that of CCD devices. However, there are enormous drawbacks with CCD devices. Two major drawbacks are that CCD device have immense power requirements, and the amount of processing circuitry required for a CCD imager always requires the use of a remote processing circuitry module which can process the image signal produced by the CCD imager. Also, because of the type of chip architecture used with CCD devices, on-chip processing is impossible. Therefore, even timing and control circuitry must be remoted from the CCD imager plane. Therefore, CCD technology is the antithesis of "camera on a chip" technology discussed below.

One particular advance in CMOS technology has been in the active pixel-type CMOS imagers which consist of randomly accessible pixels with an amplifier at each pixel site. One advantage of active pixel-type imagers is that the amplifier placement results in lower noise levels. Another major advantage is that these CMOS imagers can be mass produced on standard semiconductor production lines. One particularly notable advance in the area of CMOS imagers including active pixel-type arrays is the CMOS imager described in U.S. Pat. No. 5,471,515 to Fossum, et al. This CMOS imager can incorporate a number of other different electronic controls that are usually found on multiple circuit boards of much larger size. For example, timing circuits, and special functions such as zoom and anti-jitter controls can be placed on the same circuit board containing the CMOS pixel array without significantly increasing the overall size of the host circuit board. Furthermore, this particular CMOS imager requires 100 times less power than a CCD-type imager. In short, the CMOS imager disclosed in Fossum, et al. has enabled the development of a "camera on a chip."

Passive pixel-type CMOS imagers have also been improved so that they too can be used in an imaging device which qualifies as a "camera on a chip." In short, the major difference between passive and active CMOS pixel arrays is that a passive pixel-type imager does not perform signal amplification at each pixel site. One example of a manufacturer which has developed a passive pixel array with performance nearly equal to known active pixel devices and being compatible with the read out circuitry disclosed in the U.S. Pat. No. 5,471,515 is VLSI Vision, Ltd., 1190 Saratoga Avenue, Suite 180, San Jose, Calif. 95129. A further description of this passive pixel device may be found in applicant's patent entitled "Reduced Area Imaging Devices Incorporated Within Surgical Instruments," U.S. Pat. No. 5,986,693, and is hereby incorporated by reference.

In addition to the active pixel-type CMOS imager which is disclosed in U.S. Pat. No. 5,471,515, there have been developments in the industry for other solid state imagers which have resulted in the ability to have a "camera on a chip." For example, Suni Microsystems, Inc. of Mountain View, Calif., has developed a CCD/CMOS hybrid which combines the high quality image processing of CCDs with standard CMOS circuitry construction. In short, Suni Microsystems, Inc. has modified the standard CMOS and CCD manufacturing processes to create a hybrid process providing CCD components with their own substrate which is separate from the P well and N well substrates used by the CMOS components. Accordingly, the CCD and CMOS components of the hybrid may reside on different regions of the same chip or wafer. Additionally, this hybrid is able to run on a low power source (5 volts) which is normally not possible on standard CCD imagers which require 10 to 30 volt power supplies. A brief explanation of this CCD/CMOS hybrid can be found in the article entitled "Startup Suni Bets on Integrated Process" found in *Electronic News*, Jan. 20, 1997 issue. This reference is hereby incorporated by reference for purposes of explaining this particular type of imaging processor.

Another example of a recent development in solid state imaging is the development of a CMOS imaging sensor which is able to achieve analog to digital conversion on each of the pixels within the pixel array. This type of improved CMOS imager includes transistors at every pixel to provide digital instead of analog output that enable the delivery of decoders and sense amplifiers much like standard memory chips. With this new technology, it may, therefore, be possible to manufacture a true digital "camera on a chip." This CMOS imager has been developed by a Stanford University joint project and is headed by Professor Abbas el-Gamal.

A second approach to creating a CMOS-based digital imaging device includes the use of an over-sample converter at each pixel with a one bit comparator placed at the edge of the pixel array instead of performing all of the analog to digital functions on the pixel. This new design technology has been called MOSAD (multiplexed over sample analog to digital) conversion. The result of this new process is low power usage, along with the capability to achieve enhanced dynamic range, possibly up to 20 bits. This process has been developed by Amain Electronics of Simi Valley, Calif. A brief description of both of the processes developed by Stanford University and Amain Electronics can be found in an article entitled "A/D Conversion Revolution for CMOS Sensor?," September 1998 issue of *Advanced Imaging*. This reference is also hereby incorporated by reference for purposes of explaining these particular types of imaging processors.

Yet another example of a recent development with respect to solid state imaging is an imaging device developed by ShellCase, of Jerusalem, Israel. In an article entitled "A CSP Optoelectronic Package for Imaging and Light Detection Applications" (A. Badihi), ShellCase introduces a die-sized, ultrathin optoelectronic package which is completely packaged at the wafer level using semiconductor processing. In short, ShellCase provides a chip scale package (CSP) process for accepting digital image sensors which may be used, for example, in miniature cameras. The die-sized, ultrathin package is produced through a wafer level process which utilizes optically clear materials and completely encases the imager die. This packaging method, ideally suited for optoelectronic devices, results in superior optical performance and form factor not available by traditional image sensors. This reference is also incorporated by reference for purposes of explaining ShellCase's chip scale package process.

Yet another example of a recent development with respect to solid state imaging is shown in U.S. Pat. No. 6,020,581 entitled "Solid State CMOS Imager Using Silicon on Insulator or Bulk Silicon." This patent discloses an image sensor incorporating a plurality of detector cells arranged in an array wherein each detector cell as a MOSFET with a floating body and operable as a lateral bipolar transistor to amplify charge collected by the floating body. This reference overcomes problems of insufficient charge being collected in detector cells formed on silicon on insulator (SOI) substrates due to silicon thickness and will also work in bulk silicon embodiments.

The above-mentioned developments in solid state imaging technology have shown that "camera on a chip" devices will continue to be enhanced not only in terms of the quality of imaging which may be achieved, but also in the specific construction of the devices which may be manufactured by new breakthrough processes.

Although the "camera on a chip" concept is one which has great merit for application in many industrial areas, a need still exists for a reduced area imaging device which can be used in even the smallest type of industrial application. Recently, there have been developments with providing camera capabilities for wireless/cellular phones. Two-way still image video phones are making appearances on the market now. Additionally, there has been information regarding various worldwide manufacturers who are soon to come out with fully functional two-way video in combination with wireless/cellular phones. Because it is desirable to have a wireless/cellular phone of minimum size and weight, it is also desirable to have supporting imaging circuitry which is also of minimum size and weight. Accordingly, the invention described herein is ideal for use with upcoming video phone technology.

It is one object of this invention to provide a reduced area imaging device incorporated within a communication device which takes advantage of "camera on a chip" technology, but rearrange the circuitry in a selective stacked relationship so that there is a minimum profile presented when used within a communication device.

It is yet another object of this invention to provide imaging capability for a communication device wherein the camera used is of such small size that it can be attached to the communication device by a retractable cord which enables the imaging device to be used to image anything to which the camera is pointed at by the user without having to move the communication device away from the mouth when speaking.

It is yet another object of this invention to provide a camera with a communication device wherein the camera communicates with the communications device by a wireless link such as an RF radio link so that the camera does not have to be physically connected to the communications device. This wireless connection further enhances the capability to use the camera to shoot video without having to move the communication device or otherwise manipulate the communication device in a manner which detracts from shooting the video.

In all applications, to include use of the imaging device of this invention with a communication device, "camera on a chip" technology can be improved with respect to reducing its profile area, and incorporating such a reduced area imaging device within a communication device such that minimal size and weight is added to the communication device, and further that the imaging device can be used to image selected targets by the user.

DISCLOSURE OF THE INVENTION

In accordance with the present invention, reduced area imaging devices are provided in combination with a communication device such as a wireless/cellular phone. The term "imaging device" as used herein describes the imaging elements and processing circuitry which is used to produce a video signal which may be accepted by both a standard video device such as a television or video monitor accompanying a personal computer, and a small LCD screen which is incorporated within the video phone. The term "image sensor" as used herein describes the components of a solid state imaging device which captures images and stores them within the structure of each of the pixels in the array of pixels found in the imaging device. As further discussed below, the timing and control circuits can be placed either on the same planar structure as the pixel array, in which case the image sensor can also be defined as an integrated circuit, or the timing and control circuitry can be placed remote from the pixel array. The terms "video signal" or "image signal" as used herein, and unless otherwise more specifically defined, refer to an image which at some point during its processing by the imaging device, is found in the form of electrons which have been placed in a specific format or domain. The term "processing circuitry" as used herein refers to the electronic components within the imaging device which receive the image signal from the image sensor and ultimately place the image signal in a usable format. The terms "timing and control circuits" or "timing and control circuitry" as used herein refer to the electronic components which control the release of the image signal from the pixel array.

In a first embodiment of the communication device, the imaging device connects to the communication device by a cable or cord which may retract within the housing of the communication device. Thus in this embodiment, the camera is tethered to the communication device. In a second embodiment, the imaging device does not have to be physically connected to the imaging device; rather, a wireless RF link or other acceptable wireless technology is used so that video signals produced by the imaging device may be transmitted to and received by the communications device. One particularly advantageous wireless technology usable with the communications device of this invention is known as "Bluetooth". Another recent wireless technology which is usable with the invention is a wireless protocol known as "IEEE 802.15.3". This wireless standard is developing under the joint efforts of Kodak, Motorola, Cisco and the International Electronic and Electrical Engineers Standards Association (IEEE) Wireless Personal Area Network Working Group (WPAN). Bluetooth technology provides a universal radio interface in the 2.4 GHz frequency band that enables portable electronic devices to connect and communicate wirelessly via short-range ad hoc networks. Bluetooth radios operate in an unlicensed Instrumentation, Scientific, Medical (ISM) band at 2.4 GHz. Bluetooth is a combination of circuit and packet switching. Slots can be reserved for synchronous packets. Each packet is transmitted in a different hop frequency. A packet nominally covers a single slot, but can be extended to cover up to five slots. Bluetooth can support an asynchronous data channel, up to three simultaneous synchronous voice channels, or a channel that simultaneously supports asynchronous data and synchronous voice. Spectrum spreading is used to facilitate optional operation at power levels up to 100 mW worldwide. Spectrum spreading is accomplished by frequency hopping in 79 hops displaced by 1 MHZ, staring at 2.402 GHz and stopping at 2.480 GHz. the maximum frequency-hopping rate is 1600 hops per second. The nominal link range is 10 centimeters to 10 meters, but can be extended to more than 100 meters by increasing the transmit power. A shaped, binary FM modulation is applied to minimize transceiver complexity. The gross data rate is 1 Mb/second. A time division duplex scheme is used for full-duplex transmission. Additional technical information describing the Bluetooth global specification is found on the world wide web at www.bluetooth.com. Additional information regarding the technical specification for the IEEE 802.15.3 standard may be found at http://www. ieee802.org/15, under the link for Task Force Three (TG3).

In a first arrangement of the imaging device, the image sensor, with or without the timing and control circuitry, may be placed at the distal tip of a very small video camera module which is attached by a cable or cord to the communication device, or the camera module communicates with the communication device by a wireless RF link while the remaining processing circuitry may be placed within the housing of the communication device.

In a second arrangement of the imaging device, the image sensor and the processing circuitry may all be placed in a stacked arrangement of miniature circuit boards and positioned at the distal tip of the video camera module. In this second arrangement, the pixel array of the image sensor may be placed by itself on its own circuit board while the timing and control circuitry and processing circuitry are placed on one or more other circuit boards, or the circuitry for timing and control may be placed with the pixel array on one circuit board, while the remaining processing circuitry can be placed on one or more of the other circuit boards.

In yet another alternative arrangement of the imaging device, the pixel array, timing and control circuits, and some of the processing circuitry can be placed near the distal end of the video camera module with the remaining part of the processing circuitry being placed in the housing of the communication device.

For the arrangement or configuration of the imaging device which calls for the array of pixels and the timing and control circuitry to be placed on the same circuit board, only one conductor is required in order to transmit the image signal to the video processing circuitry. When the timing and control circuits are incorporated onto other circuit boards, a plurality of connections are required in order to connect the timing and control circuitry to the pixel array, and then the one conductor is also required to transmit the image signal to the video processing circuitry.

The invention disclosed herein can also be considered an improvement to a cellular/wireless phone wherein the improvement comprises a video system. The video system would include the video monitor attached to the phone, the camera module, the imaging device within the camera module, as well as supporting video processing circuitry for the imaging device. In yet another aspect, the invention disclosed herein can also be considered an improvement to a video telephone wherein the improvement comprises a novel imaging device, preferably of CMOS construction. For this improvement comprising the imaging device, the imaging device includes the array of pixels, and the supporting video processing circuitry for providing a video ready signal. In yet another aspect, the invention disclosed herein can also be considered an improvement to a video telephone wherein the improvement comprises an imaging device which utilizes a wireless standard in order to transmit video images to the video telephone.

The video ready signal produced by the video processing circuitry may be of differing video formats for viewing on different types of video devices. For example, the video ready signal may be a NTSC/PAL compatible video signal for viewing on a remote video device such as a TV; the video signal may be a YUV 4:2:2 signal for viewing on a video monitor attached to the phone; and/or the video signal may be VGA compatible for viewing on a personal computer. Accordingly, the invention disclosed herein has utility with respect to an overall combination of elements, as well as various sub-combination of elements.

BRIEF DESCRIPTION OF THE DRAWINGS

FIG. 1 is an enlarged fragmentary partially exploded perspective view of the distal end of the camera module which is used in conjunction with the communication device, specifically illustrating the arrangement of the image sensor with respect to the other elements of the camera module;

FIG. 1a is an enlarged exploded perspective view illustrating another configuration of the image sensor wherein video processing circuitry is placed behind and in longitudinal alignment with the image sensor;

FIG. 2 is a perspective view of the communication device in a first embodiment incorporating the reduced area imaging device of this invention, and further illustrating the video monitor in operation, along with the camera module pulled out in the extended position;

FIG. 3 illustrates the communication device of FIG. 2 wherein the camera module is in the retracted position, along with the video monitor in the folded or retracted position;

FIG. 4 is another perspective view of the communication device of this invention in the first embodiment illustrating an alternative arrangement for placement of the video monitor within a flip panel;

FIG. 5 is a perspective view of the communication device of FIG. 4 illustrating the alternative arrangement of the video monitor with the video monitor stored within the folded flip panel;

FIG. 7 is a perspective view of the communication device in a second embodiment wherein the camera module utilizes a wireless technology, thus the camera module may be physically separated from the communication device during operation, but can still be housed within the communication device for storage and for recharge of the battery of the camera module;

FIG. 8 is an overall schematic diagram, similar to FIG. 6, of the functional components which make up the communication device and a simplified cross sectional view of the camera module in the second preferred embodiment wherein the camera module communicates with the communication device via a wireless link;

FIG. 8a is an enlarged view of some of the components of the camera module, specifically, the components used in the wireless link with the communication device;

FIG. 9 is a more detailed schematic diagram of the functional electronic components which make up the imaging device;

FIG. 9a is an enlarged schematic diagram of a circuit board/planar structure which may include the array of pixels and the timing and control circuitry;

BEST MODE FOR CARRYING OUT THE INVENTION

Figure 6:
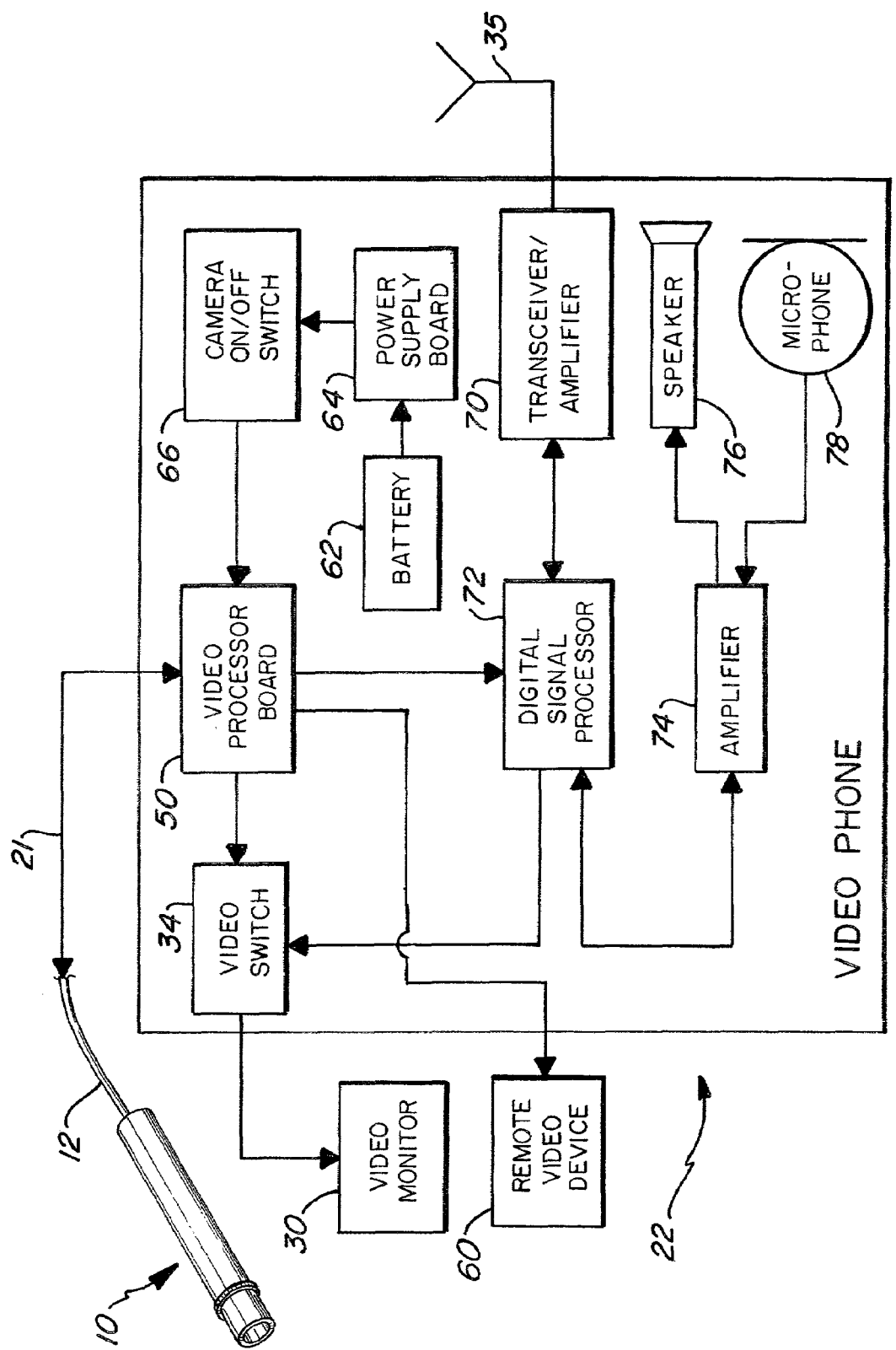
FIG. 6 is an overall schematic diagram of the functional electronic components in the first embodiment which make up both the communication device, and the reduced area imaging device.

In accordance with the invention, as shown in FIG. 1, a camera module 10 is provided which incorporates a reduced area imaging device 11. As further discussed below, the elements of the imaging device 11 may all be found near one location, or the elements may be separated from one another and interconnected by the appropriate wired connections. The array of pixels making up the image sensor captures images and stores them in the form of electrical energy by conversion of light photons to electrons. This conversion takes place by the photo diodes in each pixel which communicate with one or more capacitors which store the electrons. Specifically, the camera module 10 includes an outer tube/sheath 14 which houses the components of the imaging device. The camera module is shown as being cylindrical in shape having a window 16 sealed at the distal end of the camera module. A retractable cable 12 extends from the proximal end of the camera module 10. A shielded cable 21 is used to house the conductors which communicate with the imaging device 11. The shielded cable 21 is then housed within the retractable cable 12. A lens group 18 is positioned at the distal end of the camera module to enable an image to be appropriately conditioned prior to the image impinging upon the imaging device 11. Also shown is a focusing ring 20 which enables the lens group 18 to be displaced distally or proximally to best focus an image on the imaging device 11.

Now referring to FIGS. 2–5, a video phone 22 in a first embodiment is shown which incorporates the camera module 10. In basic terms, the video phone is simply a standard wireless/cellular phone which has added thereto the ability to send and receive video signals which may both be viewed on video monitor 30. Beginning first with a description of the basic components of the video phone, it includes a phone housing 24 which holds the components of the video phone. Cable 12 is housed within the housing 24 when in the retracted position. A spring biased spool (not shown) or some other known retracting device is mounted within the housing 24 enabling the cable 12 to be extended or retracted. When the cable is retracted, the camera module 10 can be stored within cavity or opening 25 at the base of housing 24. This cavity or opening 25 can substantially conform to the size and shape of the camera module 10. The camera module 10 is illustrated as being elongate and cylindrical, minimizing its size and profile, and enhancing its ability to be stored within opening 25. As shown in FIG. 3, when the camera module 10 is stored, it does not increase the overall size of the video telephone 22, and does not protrude away from the phone housing 24, thus making the camera module 10 a component which truly integrates with the housing 24 of the video phone 22. The cable 12 is of a selected length which allows the user to point the camera module 10 toward a targeted object to taking video. A keypad 26 is provided enabling a user to dial the phone, or achieve other well-known telephone functions. An audio receiving assembly 27 in the conventional manner is provided which allows the user to listen to incoming audio. This assembly may later be referred to simply as a speaker. An orifice or hole 28 is provided which communicates with a microphone (discussed below) for transmitting audio signals. The phone display 29 displays the various functions of the phone as controlled by a user. The display 29 in most wireless/cellular phones is a liquid crystal display. The video monitor 30 attaches to the housing 24 as by linkage 31. As shown, two pieces of linkage are provided, along with three ball/socket type joints 32 which enable the video monitor to be articulated to the desired position with respect to the housing 24. An internal video cable 33 having a plurality of conductors (not shown) extends through the linkage 31 and the ball and socket joints 32 for providing the video signals which are displayed on the video monitor 30. The video monitor 30 may be a liquid crystal display (LCD) type, or any other well-known display device of high resolution which has low power requirements, and has minimum size requirements as well. An example of a manufacture of such a miniature LCD monitor includes DISPLAYTECH of Longmont, Colo. DISPLAYTECH manufactures a miniature reflective display that consists of ferroelectric liquid crystal (FLC) applied to a CMOS integrated circuit. The reflective display is a VGA display panel having low voltage digital operation, low power requirements, and full color operation. One of their specific products includes the LightCasterÔ VGA Display Panel, Model LDP-0307-MV1. This is but one example of an LCD monitor which is available and usable within the invention herein described. As further discussed below, a video select switch 34 is mounted on the housing 24 which enables a user to select viewing of either incoming video signals, or to view the outgoing video signals which are those images taken by the camera module 10. A conventional antenna 35 is provided to enhance reception and transmission capabilities of the video phone.

FIGS. 4 and 5 illustrate a modification of the video phone of FIGS. 2 and 3. Specifically, FIGS. 4 and 5 illustrate an alternative way in which to attach the video monitor 30 to the video phone 22. As shown, FIGS. 4 and 5 illustrate a flip panel 36 which attaches to the base of the housing 24 as by hinge 39. The video monitor itself is then mounted to the flip panel 36 as by hinge 37. Video signals are transmitted to the video monitor 30 of FIGS. 4 and 5 by the conductors housed in video cable 33. As shown, video cable 33 is routed through the flip panel 36. The video monitor 30 of FIGS. 4 and 5 can be placed in the desired position by rotating the flip panel 36 about hinge 39, and then rotating the video monitor 30 about hinge 37.

Referring back to FIGS. 1 and 1a, the imaging device 11 includes an image sensor 40. FIG. 1 illustrates that the image sensor 40 can be a planar and square shaped member, or alternatively, planar and circular shaped to better fit within outer tube 14. In the configuration of the imaging device in FIGS. 1 and 1a, there are only three conductors which are necessary for providing power to the image sensor 40, and for transmitting an image from the image sensor 40 back to the processing circuitry found within the phone housing 24. Specifically, there is a power conductor 44, a grounding conductor 46, and an image signal conductor 48, each of which are hardwired to the image sensor 40. Thus, shielded cable 21 may simply be a three conductor, 50 ohm type cable.

Image sensor 40 can be as small as 1 mm in its largest dimension. However, a more preferable size for most video phone applications would be between 4 mm to 8 mm in the image sensor's largest dimension (height or width). The image signal transmitted from the image sensor 40 through conductor 48 is also herein referred to as a pre-video signal. Once the pre-video signal has been transmitted from image sensor 40 by means of conductor 48, it is received by video processing board 50, as shown in FIG. 6. Video processing board 50 then carries out all the necessary conditioning of the pre-video signal and places it in a form, also referred to herein as a video ready signal, so that it may be viewed directly on a remote video device such as a television or standard computer video monitor. In order for the pre-video signal to be viewed on the monitor 30, the pre-video signal is further conditioned by a digital signal processor 72, as further discussed below. The video signal produced by the video processing board 50 which is viewable by an NTSC/PAL compatible video device (such as a television) can be further defined as a post-video signal.

FIG. 1 illustrates an arrangement wherein the image sensor 40 is placed by itself adjacent the distal end of the camera module 10. Alternatively, some or all of the video processing circuitry may be placed in adjacent circuit boards directly behind the image sensor 40.

Accordingly, FIG. 1a illustrates video processor board 50 aligned directly behind the image sensor 40. A plurality of pin connectors 52 can be used to interconnect image sensor 40 to video processor board 50. Depending upon the specific configuration of image sensor 40, pin connectors 52 may be provided for structural support and/or to provide a means by which image signals are transmitted between image sensor 40 and board 50. Additionally, digital signal processor 72 could also be placed behind image sensor 40 and behind video processing board 50. Accordingly, the image sensor, and all supporting video processing circuitry could be placed at the distal end of the camera module 10. However, because of the ample space within housing 24, it may be preferable to place at least some of the video processing circuitry within housing 24. In the case of FIG. 1a, the conductor 49 represents the conductor which may carry the post-video signal for direct connection with a remote video device 60 such as a television or computer monitor. As also discussed further below with respect to the first embodiment, placement of the digital signal processor 72 at the distal tip of the camera module behind the video processing board 50 would also enable yet another conductor (not shown) to connect directly to the video monitor 30 for transmitting a video ready signal to the video monitor 30.

Again referring to FIG. 1, the area which is occupied by image sensor 40 may be defined as the profile area of the imaging device and which determines its critical dimensions. If it is desired to place video processing circuitry adjacent the image sensor 40 at the distal end of the camera module 10, such circuitry must be able to be placed on one or more circuit boards which are longitudinally aligned with image sensor 40 along longitudinal axis XX. If it is not important to limit the size of the profile area, then any circuitry placed behind image sensor 40 can be aligned in an offset manner, or may simply be larger than the profile area of image sensor 40. In the configuration shown in FIG. 1a, it is desirable that elements 40 and 50 be approximately the same size so that they may uniformly fit within the distal end of outer tube 14.

Now referring to the first embodiment of FIG. 6, a further explanation is provided of the basic electronic components of the video phone 22 which combines circuitry and functionality of a standard mobile/wireless phone and a video system. One example of a patent disclosing basic mobile phone technology including a discussion of basic phone circuitry is U.S. Pat. No. 6,018,670. This patent is hereby incorporated by reference in its entirety for purposes of disclosing standard or basic mobile phone technology and supporting circuitry. As shown in FIG. 6, a conventional cellular phone battery 62 is provided which communicates with power supply board 64. Power supply board 64 conditions various power outputs to the components of the device, to include power to the video components. In the preferred imaging device of this invention, the power to the imaging device may simply be direct current of between about 1.5 to 12 volts, depending upon the power requirements of the imaging device. A camera on/off switch 66 is set to the "on" position in order to activate the camera module 10. The video processor board 50 then transfers power to supplies the camera module 10, and also receives the analog pre-video signal back from the camera module, as further discussed below. After processing of the pre-video signal at the video processor board 50, the video signal is video ready, meaning that it may then be directly viewed on a remote compatible video device 60, such as a television or computer monitor. The video processor board 50 in FIGS. 6 and 8 is shown as residing within the housing 24; however, as discussed above with respect to the various arrangements of the imaging device, it can also be located within the distal tip of the camera module. A video port 54 can be provided on the housing 24 enabling a user to take a standard video jack and interconnect the video phone with the video port of the remote video device. The video format for such remote video devices includes NTSC/PAL and VGA; thus, the video signal processed by video processor board 50 creates the video ready signals for use with these remote video devices. For purposes of viewing images on the monitor 30, the pre-video signal is further processed into a digital format within video processor board 50, preferably an 8 bit composite video signal format that is commonly referred to as "YUV 4:2:2." This video format easily lends itself to video compression. This 8 bit digital video signal is then sent to the digital signal processor 72 which performs two functions relevant to the video signal. The digital signal processor 72 further converts the signal into a format that is compatible with the driver circuitry of the video monitor 30. Secondly, the digital signal processor 72 compresses the YUV signal using a common video compression format, preferably JPEG. The JPEG encoded video signal is then mixed with the audio signal created by microphone 78 and amplifier 74, and the resulting high frequency carrier signal may then be passed onto the transceiver/amplifier section 70 for transmission. The transceiver/amplifier section also modulates the carrier signal prior to transmission. Depending upon the position of video switch 34, the video signal from digital signal processor 72 is either sent to the monitor 30, or is sent to the transceiver/amplifier section 70 for transmission. As also shown, the antenna 35 is used for enhancement of reception and transmission of transmitted and received carrier signals.

The transceiver/amplifier section 70 also serves as a receiver which receives an incoming carrier signal. This incoming signal is then demodulated within section 70, the video and audio components of the incoming signal are separated, and then these separated signals are then sent to the digital signal processor 72 which performs video decompression. Then, the decompressed video signal is sent to the monitor 30 for viewing (if the video switch 34 is placed in that selected mode). The decompressed audio signal is sent to the amplifier 74, and then to the speaker 76. The video switch 34 may simply be a momentary, spring loaded, push button-type switch. When the video switch 34 is not depressed, incoming video, which is received via the handset antenna 35, is processed as discussed above in the transceiver/amplifier section 70 and digital signal processor 72, and then sent to the monitor 30. When the video switch 34 is depressed and held, the video signal produced from the camera module 10 is processed as discussed above, and ultimately sent to the monitor 30. An operator can cycle the switch 34 between the two positions in order to selectively choose whether to view incoming or outgoing video.

To summarize the operation of the video telephone, a user wishing to contact another party would dial the telephone in the conventional manner. Assuming the party called has video telephone capability, the user could view the images transmitted from the other party by not depressing the video switch 34. If the user desires to transmit video images to the other party, the user would grasp the camera module 10, and extend the cord 12 of the camera module by pulling it away from the video telephone, and then point the camera module at the object/person targeted. The user then depresses the video switch 34 which results in transmission of the images captured by the camera module 10 to the other party. Also, the video monitor 30 will display the images captured by the camera module 10 by depressing the video switch 34. Because the camera module is tethered to the video telephone by retractable cable 12, the user can continue a conversation with the other party without having to physically remove the video telephone away from the user's mouth when simultaneously taking video by the camera module. Because of the extremely small size of the camera module 10, it is easily housed within the housing 24 when not in use.

Now referring to FIG. 7, the second embodiment of the communication device is illustrated which utilizes a wireless camera module 10'. As with the first embodiment, the camera module 10' is cylindrical shaped and can be stored within hole or orifice 25.

Thus, exteriorly, the communication device 22 appears the same, along with camera module 10' with the exception that there is no cable or cord interconnecting the camera module 10' to the communication device 22. Now also referring to FIGS. 8 and 8a, in lieu of a wired connection, the camera module 10' communicates with the communication device 22 by a transceiver radio element 88 which is mounted in the proximal end of the module 10'. Similarly, the communication device 22 also includes its own transceiver radio module 84 which allows video signals transmitted by transceiver 88 to be received and then passed on to the video processor board 50 for further video signal processing, as necessary. Antennae 85 communicates with transceiver module 84 for enhancing reception of incoming video signals from the camera module 10'. The camera module 10' also has its own antennae 81 which enhances reception for authenticating signals which may be transmitted by transceiver 84. As understood by those skilled in the art, Bluetooth and other RF standards involve two-way communications whereby transmissions are authenticated and synchronized. Thus the transceiver module 84 whose main function is to receive a signal from the camera module 10', also transmits some signals to the camera module 10' and camera module 10' also acts as a receiver to authenticate and receive such signals. The proximal end of the camera module 10' also includes a rechargeable battery 82 which is recharged when the module 10' is seated within the opening 25 of the communication device 22. The battery 82 can be a common rechargeable nickel-cadmium or lithium-ion type battery. The battery 82 has a contact 83 protruding from the proximal tip of the camera module 10'. The deepest portion of chamber/opening 25 also has a contact 87 (shown schematically in FIG. 7) which makes contact with contact 83 when the camera module 10' is placed in the chamber. Contact 87 electrically couples with camera battery charging circuit 86 which provides an electrical charge for recharging the battery 82. When the camera module 10' is placed in the chamber 25, the external housing or casing of the camera module 10' is electrically conductive and contacts a ground such as spring loaded clip (not shown) within the chamber 25. Thus, recharge of the battery 82 can be accomplished.

As shown in FIG. 7, the charge circuit 86 receives power from power supply board 64. Thus, the battery 62 of the communication device also provides recharging capability to the battery 82.

The operation of the communication device is essentially the same in the second embodiment. If the user desires to transmit video images to another party, the user would grasp the camera module 10', remove it from chamber 25, and then point it at the target. The camera module 10' collects the video images through the objective lens group 18 which conditions images received by the image sensor 40. The plurality of conductors housed in the shielded miniature cable 21 transfers the video signals to the transceiver radio element 88. The transceiver radio element 88, among other functions, adds a high frequency carrier signal and baseband protocol to the video signal which is then transmitted to the transceiver radio module 84. The video signal transmitted by the transceiver radio element 88 is authenticated by the transceiver radio module 84, the video signal is stripped of its carrier, and then routed by a link controller (not shown as a separate element apart from transceiver 84) to the video processor circuitry 50. The video signal is then handled in the same manner as the first embodiment. The user would depress the video switch 34 to initiate transmission of the video to the other party of the telephone call. Once the camera module 10' is removed from its seated position in the chamber 25, the contact between contacts 83 and 87 is broken. This break in electrical contact would allow the battery 82 to energize the camera module 10', and thus allow the camera module 10' to begin wirelessly communicating with the transceiver radio module 84. The user would be able to easily hold and point the camera module 10' with one hand, while operating the communication device 22 in the other hand. As with the first embodiment, the video monitor 30 would display the video images simultaneously while video images were being transmitted to the other party so long as video switch 34 was depressed. If the user wished to receive video images transmitted from the other party, the user would simply reset the video switch 34 to its off or inactive state. The camera module 10' would continue to shoot video and communicate with the module 84; however, the video images would not be seen on screen 30. Again as with the first embodiment, a remote video device 60 could receive video images and remotely display and record the same.

Although FIG. 8 illustrates the video processor board 50 located within the communication device 22, the video processor board 50 may alternatively be co-located with the imaging device 40 within the distal tip of the camera module 10'. Accordingly, all necessary video processing may take place within the camera module and the video signal which would be transmitted by the radio transceiver element 88 is a post video signal which is ready for viewing by either the video monitor 30, or the remote video device 60 once the transceiver radio module 84 receives, authenticates, and strips the video signal of its carrier frequency as transmitted by the radio transceiver element 88.

FIG. 9 is a schematic diagram illustrating one way in which the imaging device 11 may be constructed. As illustrated, the image sensor 40 may include the timing and control circuits on the same planar structure. Power is supplied to image sensor 40 by power supply board 64. The connection between image sensor 40 and board 64 may simply be a cable having two conductors therein, one for ground and another for transmitting the desired voltage. These are illustrated as conductors 44 and 46. The output from image sensor 40 in the form of the pre-video signal is input to video processor board 50 by means of the conductor 48. In the configuration of FIG. 4, conductor 48 may simply be a 50 ohm conductor. Power and ground also are supplied to video processing board 50 by conductors 44 and 46 from power supply board 52. The output signal from the video processor board 50 is in the form of the post-video signal and which may be carried by conductor 49 which can also be a 50 ohm conductor. As discussed above with respect to the second embodiment, in lieu of a hard wired connection by use of conductors 48 and 49, the pre-video signal or the post-video signal (depending upon the configuration of the imaging device) is transmitted wirelessly to the transceiver radio module 84.

Although FIG. 9 illustrates the image sensor and the timing and control circuits being placed on the same circuit board or planar structure, it is possible to separate the timing and control circuits from the pixel array and place the timing and control circuits onto video processing board 50. The advantage in placing the timing and control circuits on the same planar structure as the image sensor is that only three connections are required between image sensor 40 and the rest of the imaging device, namely, conductors 44, 46 and 48. Additionally, placing the timing and control circuits on the same planar structure with the pixel array results in the pre-video signal having less noise. Furthermore, the addition of the timing and control circuits to the same planar structure carrying the image sensor only adds a negligible amount of size to one dimension of the planar structure. If the pixel array is to be the only element on the planar structure, then additional connections must be made between the planar structure and the video processing board 50 in order to transmit the clock signals and other control signals to the pixel array. For example, a ribbon-type cable (not shown) or a plurality of 50 ohm coaxial cables (not shown) must be used in order to control the downloading of information from the pixel array. Each of these additional connections would be hard wired between the boards.

FIG. 9a is a more detailed schematic diagram of image sensor 40 which contains an array of pixels 90 and the timing and control circuits 92. One example of a pixel array 90 which can be used within the invention is similar to that which is disclosed in U.S. Pat. No. 5,471,515 to Fossum, et al., said patent being incorporated by reference herein. More specifically, FIG. 3 of Fossum, et al. illustrates the circuitry which makes up each pixel in the array of pixels 90. The array of pixels 90 as described in Fossum, et al. is an active pixel group with intra-pixel charged transfer. The image sensor made by the array of pixels is formed as a monolithic complementary metal oxide semiconductor (CMOS) integrated circuit which may be manufactured in an industry standard complementary metal oxide semiconductor process. The integrated circuit includes a focal plane array of pixel cells, each one of the cells including a photo gate overlying the substrate for accumulating the photo generated charges. In broader terms, as well understood by those skilled in the art, an image impinges upon the array of pixels, the image being in the form of photons which strike the photo diodes in the array of pixels. The photo diodes or photo detectors convert the photons into electrical energy or electrons which are stored in capacitors found in each pixel circuit. Each pixel circuit has its own amplifier which is controlled by the timing and control circuitry discussed below. The information or electrons stored in the capacitors is unloaded in the desired sequence and at a desired frequency, and then sent to the video processing board 50 for further processing.

Although the active pixel array disclosed in U.S. Pat. No. 5,471,515 is mentioned herein, it will be understood that the hybrid CCD/CMOS described above, or any other solid state imaging device may be used wherein timing and control circuits can be placed either on the same circuit board or planar structure with the pixel array, or may be separated and placed remotely. Furthermore, it will be clearly understood that the invention claimed herein is not specifically limited to an image sensor as disclosed in the U.S. Pat. No. 5,471,515, but encompasses any image sensor which may be configured for use in conjunction with the other processing circuitry which makes up the imaging device of this invention.

To summarize the different options available in terms of arrangement of the components of the imaging device 11, the array of pixels 90 of the image sensor 40 may be placed alone on a first plane, or the timing and control circuitry 92 may be placed with the array of pixels 90 on the first plane. If the timing and control circuitry 92 is not placed with the array of pixels 90 on the first plane, the timing and control circuitry 92 may be placed by itself on a second plane, or the timing and control circuitry 92 may be placed on a second plane with some or all of the processing circuitry from video processing board 50. The video processing board 50 itself may be placed on one or more planes on corresponding circuit boards containing video processing circuitry. FIG. 1a illustrates a single video processor board 50 located directly behind image sensor 40; however, it shall be understood that additional circuit boards containing additional circuitry may be placed behind the image sensor 40 and behind the video processing board 50. Some or all of the video processing circuitry may be placed within the camera module 10 near the distal end thereof adjacent the image sensor 40. Video processing circuitry which is not placed within the distal end of the camera module 10 may be placed within the housing 24 of the communication device. If video processing circuitry is placed near the distal end of the camera module 10, it is preferable to arrange the video processing circuitry in a stacked relationship behind the image sensor 40. Additionally, it is preferable to place the processing circuitry in a parallel arrangement with respect to image sensor 40 and to center such video processing circuitry along axis X—X in order to minimize the size of camera module 10.

The timing and control circuits 92 are used to control the release of the image information or image signal stored in the pixel array. In the image sensor of Fossum, et al., the pixels are arranged in a plurality of rows and columns. The image information from each of the pixels is first consolidated in a row by row fashion, and is then downloaded from one or more columns which contain the consolidated information from the rows. As shown in FIG. 9a, the control of information consolidated from the rows is achieved by latches 94, counter 96, and decoder 98. The operation of the latches, counter and decoder is similar to the operation of similar control circuitry found in other imaging devices. That is, a latch is a means of controlling the flow of electrons from each individual addressed pixel in the array of pixels. When a latch 94 is enabled, it will allow the transfer of electrons to the decoder 98. The counter 96 is programmed to count a discrete amount of information based upon a clock input from the timing and control circuits 92. When the counter 96 has reached its set point or overflows, the image information is allowed to pass through the latches 94 and be sent to the decoder 98 which places the consolidated information in a serial format. Once the decoder 98 has decoded the information and placed it in the serial format, then the row driver 100 accounts for the serial information from each row and enables each row to be downloaded by the column or columns. In short, the latches 94 will initially allow the information stored in each pixel to be accessed. The counter 96 then controls the amount of information flow based upon a desired time sequence. Once the counter has reached its set point, the decoder 98 then knows to take the information and place it in the serial format. The whole process is repeated, based upon the timing sequence that is programmed. When the row driver 100 has accounted for each of the rows, the row driver reads out each of the rows at the desired video rate.

The information released from the column or columns is also controlled by a series of latches 102, a counter 104 and a decoder 106. As with the information from the rows, the column information is also placed in a serial format which may then be sent to the video processing board 50. This serial format of column information is the pre-video signal carried by conductor 48. The column signal conditioner 108 places the column serial information in a manageable format in the form of desired voltage levels. In other words, the column signal conditioner 108 only accepts desired voltages from the downloaded column(s).

The clock input to the timing and control circuits 92 may simply be a quartz crystal timer. This clock input is divided into many other frequencies for use by the various counters. The run input to the timing and control circuit 92 may simply be an on/off control. The default input can allow one to input the pre-video signal to a video processor board which may run at a frequency of other than 30 hertz. The data input controls functions such as zoom. At least for a CMOS type active pixel array which can be accessed in a random manner, features such as zoom are easily manipulated by addressing only those pixels which locate a desired area of interest by the user.

A further discussion of the timing and control circuitry which may be used in conjunction with an active pixel array is disclosed in U.S. Pat. No. 5,471,515 and is also described in an article entitled "Active Pixel Image Sensor Integrated With Readout Circuits" appearing in *NASA Tech Briefs*, October 1996, pp. 38 and 39. This particular article is also incorporated by reference.

Figure 9B:
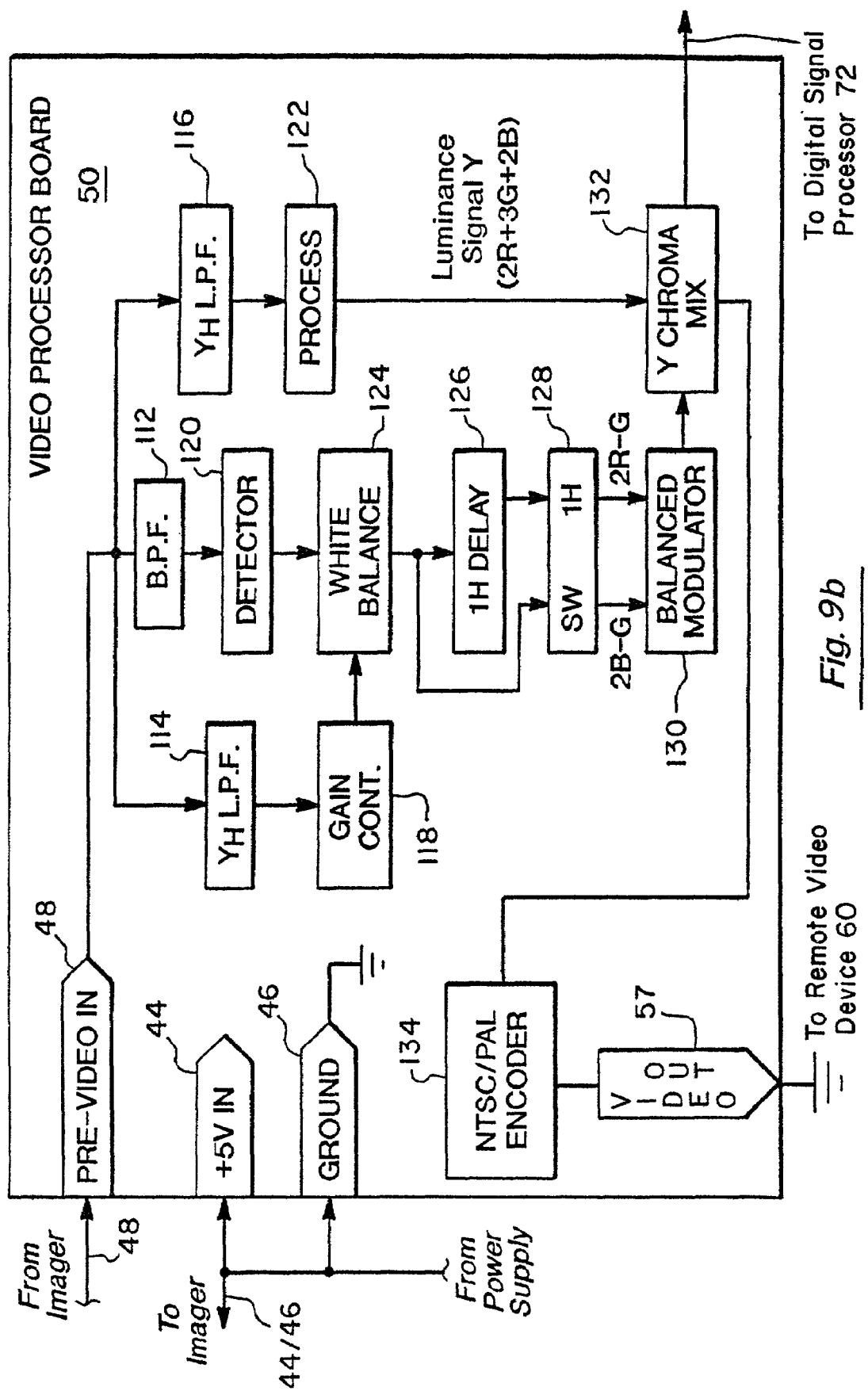
FIG. 9b is an enlarged schematic diagram of a video processing board/planar structure having placed thereon the processing circuitry which processes the pre-video signal generated by the array of pixels and which converts the pre-video signal to a post-video signal which may be accepted by an NTSC/PAL compatible video device.

Once image sensor 40 has created the pre-video signal, it is sent to the video processing board 50 for further processing. At board 50, as shown in FIG. 9b, the pre-video signal is passed through a series of filters. One common filter arrangement may include two low pass filters 114 and 116, and a band pass filter 112. The band pass filter only passes low frequency components of the signal. Once these low frequency components pass, they are then sent to detector 120 and white balance circuit 124, the white balance circuit distinguishing between the colors of red and blue. The white balance circuit helps the imaging device set its normal, which is white. The portion of the signal passing through low pass filter 114 then travels through gain control 118 which reduces the magnitude or amplitude of this portion to a manageable level. The output from gain control 118 is then fed back to the white balance circuit 124. The portion of the signal traveling through filter 116 is placed through the processor 122. In the processor 122, the portion of the signal carrying the luminance or non-chroma is separated and sent to the Y chroma mixer 132. Any chroma portion of the signal is held in processor 122.

Referring to the output of the white balance circuit 124, this chroma portion of the signal is sent to a delay line 126 where the signal is then further reduced by switch 128. The output of switch 128 is sent through a balanced modulator 130 and also to the Y chroma mixer 132 where the processed chroma portion of the signal is mixed with the processed non-chroma portion. Finally, the output from the Y chroma mixer 132 is sent to the NTSC/PAL encoder 134, commonly known in the art as a "composite" encoder. The composite frequencies are added to the signal leaving the Y chroma mixer 132 in encoder 134 to produce the post-video signal which may be accepted by a television. Additionally, the signal from Y chroma mixer 132 is sent to the digital signal processor 72 so that images can be viewed on monitor 30.

In addition to the functions described above that are achieved by the digital signal processor 72, the processor 72 can also provide additional digital enhancements. Specifically, digital enhancement can sharpen or otherwise clarify the edges of an image viewed on a video screen which might normally be somewhat distorted. Additionally, selected background or foreground images may be removed thus only leaving the desired group of images.

In addition to digital enhancement, the digital signal processor 72 can include other circuitry which may further condition the signal received from board 50 so that it may be viewed in a desired format other than NTSC/PAL. One common encoder which can be used would be an RGB encoder. An RGB encoder separates the signal into the three primary colors (red, green and blue). A SVHS encoder (super video home system) encoder could also be added to processor 72. This type of encoder splits or separates the luminance portion of the signal and the chroma portion of the signal. Some observers believe that a more clear signal is input to the video device by such a separation, which in turn results in a more clear video image viewed on the video device. Another example of an encoder which could be added to processor 72 includes a VGA compatible encoder, which enables the video signal to be viewed on a standard VGA monitor which is common to many computer monitors.

One difference between the arrangement of image sensor 40 and the outputs found in FIG. 3 of the Fossum, et al. patent is that in lieu of providing two analog outputs [namely, VS out (signal) and VR out (reset)], the reset function takes place in the timing and control circuitry 92. Accordingly, the pre-video signal only requires one conductor 48.

FIGS. 10 a–10e illustrate in more detail one example of circuitry which may be used in the video processing board 50 in order to produce a post-video signal which may be directly accepted by a NTSC/PAL compatible video device such as a television. The circuitry disclosed in FIGS. 10a–10e is very similar to circuitry which is found in a miniature quarter-inch Panasonic camera, Model KS-162. It will be understood by those skilled in the art that the particular arrangement of elements found in FIGS. 10a–10e are only exemplary of the type of video processing circuitry which may be incorporated in order to take the pre-video signal and condition it to be received by a desired video device.

Figure 10A:
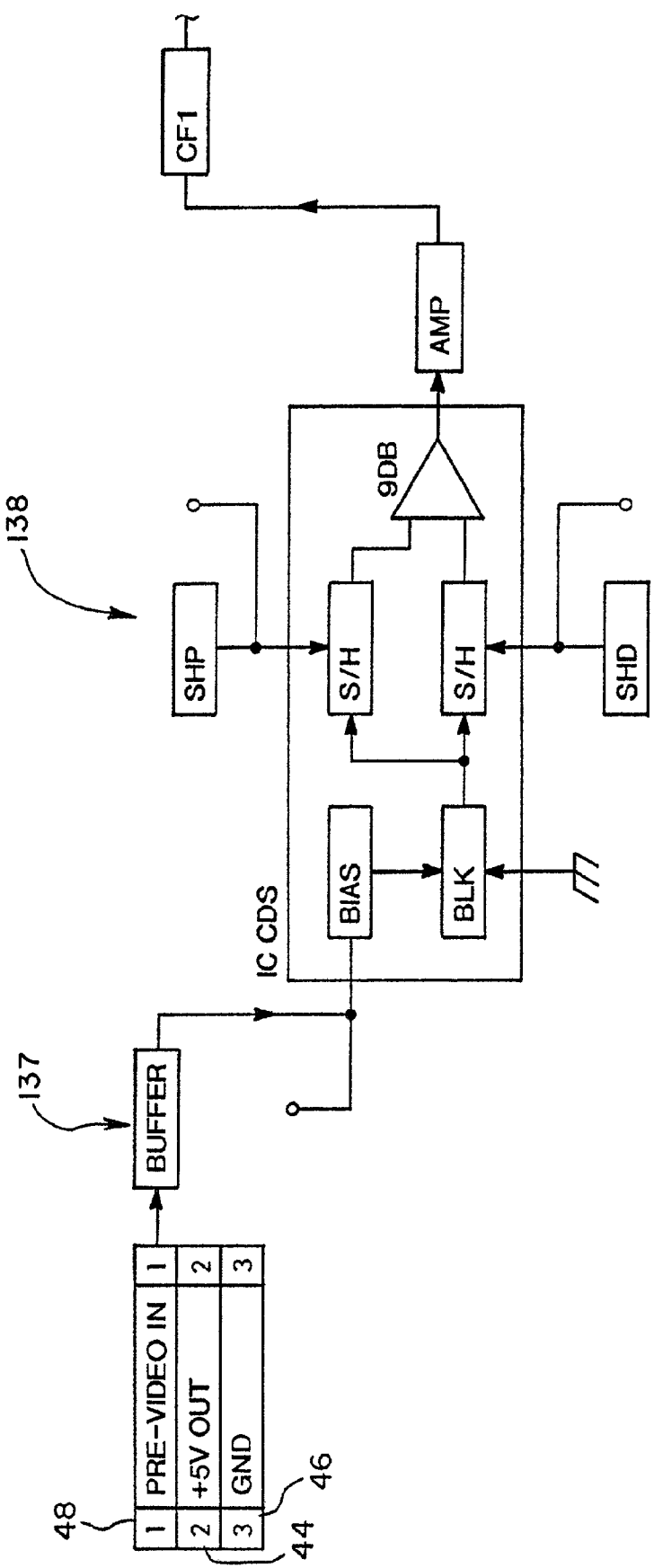
FIGS. 10a–10e are schematic diagrams that illustrate an example of specific circuitry which may be used to make the video processing circuitry of the imaging device.

As shown in FIG. 10a, 5 volt power is provided along with a ground by conductors 44 and 46 to board 50. The pre-video signal carried by conductor 48 is buffered at buffer 137 and then is transferred to amplifying group 138. Amplifying group 138 amplifies the signal to a usable level as well as achieving impedance matching for the remaining circuitry.

Figure 10B:
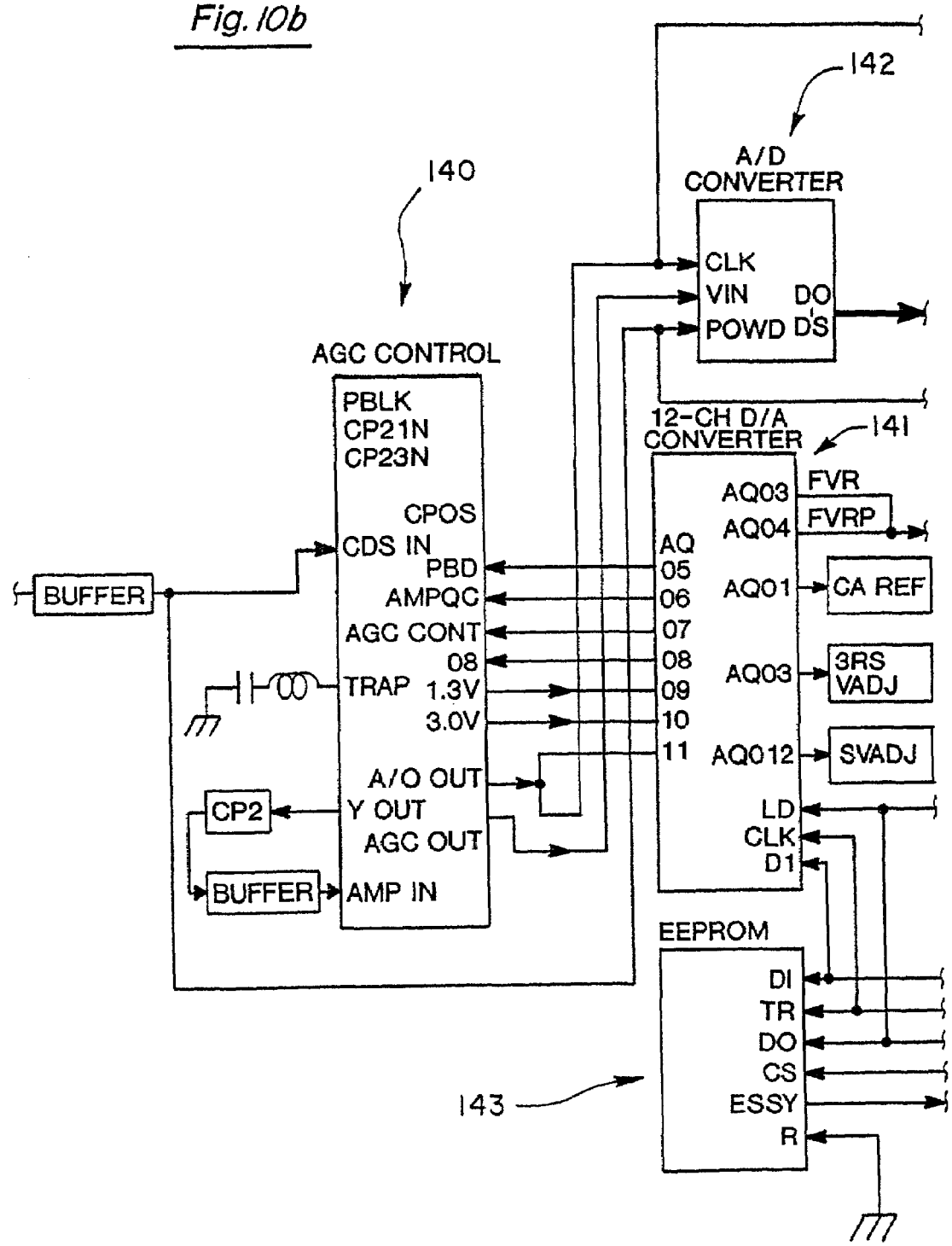

The next major element is the automatic gain control 140 shown in FIG. 10b. Automatic gain control 140 automatically controls the signal from amplifying group 138 to an acceptable level and also adds other characteristics to the signal as discussed below. More specifically, automatic gain control 140 conditions the signal based upon inputs from a 12 channel digital to analog converter 141. Converter 141 retrieves stored information from EEPROM (electrically erasable programmable read only memory) 143. EEPROM 143 is a non-volatile memory element which may store user information, for example, settings for color, tint, balance and the like. Thus, automatic gain control 140 changes the texture or visual characteristics based upon user inputs. The keypad 26, in addition to the conventional buttons used to control telephone communications, could also include buttons for controlling the image viewed on monitor 30 such as a gain control 140. The signal leaving the automatic gain control 140 is an analog signal until being converted by analog to digital converter 142.

Figure 10C:
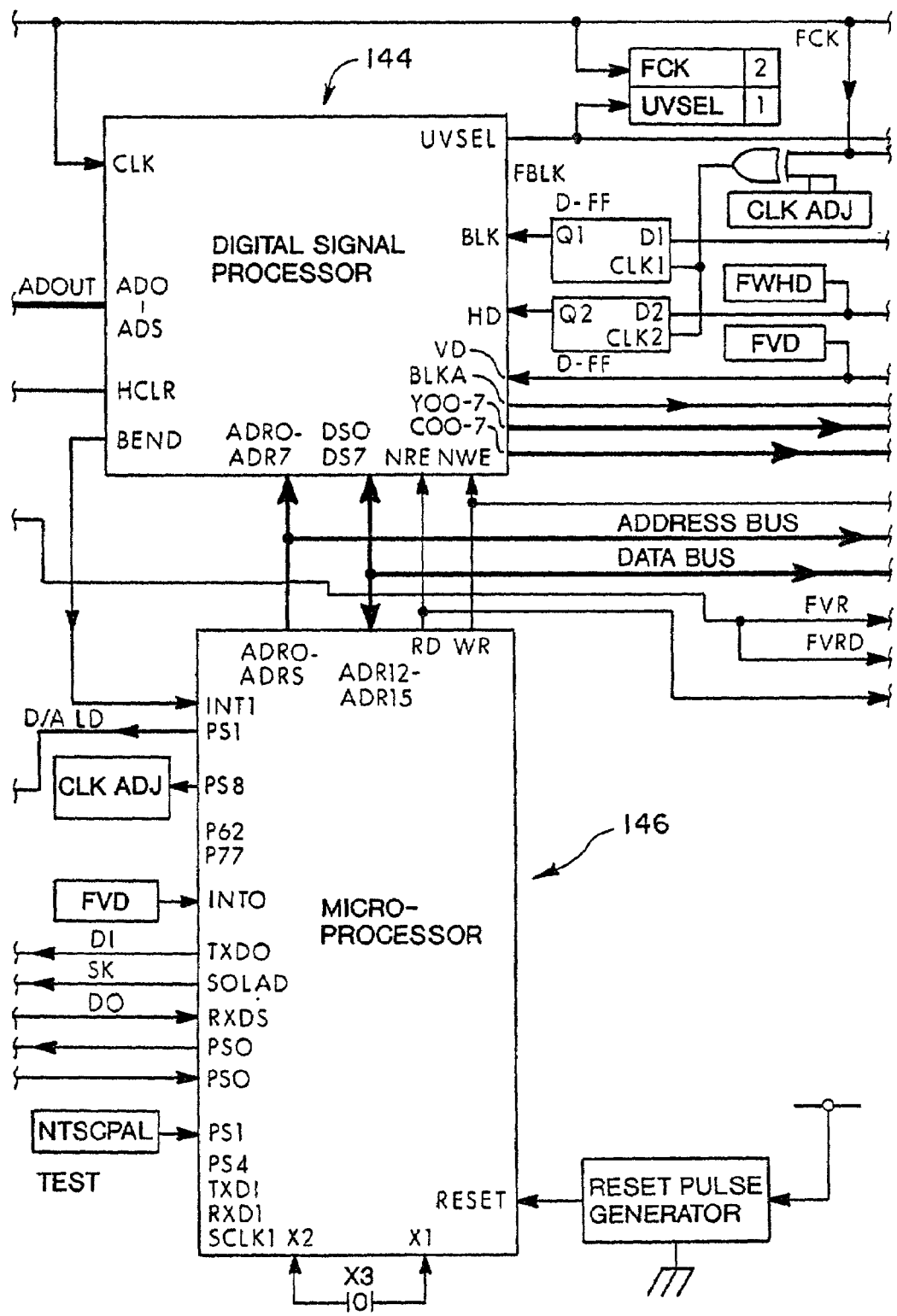

Digital signal processor 144 of FIG. 10c further processes the converted signal into a serial type digital signal. One function of the microprocessor 146 is to control the manner in which digital signal processor 144 sorts the digital signals emanating from converter 142. Microprocessor 146 also controls analog to digital converter 142 in terms of when it is activated, when it accepts data, when to release data, and the rate at which data should be released. Microprocessor 146 may also control other functions of the imaging device such as white balance. The microprocessor 146 may selectively receive the information stored in the EEPROM 143 and carry out its various commands to further control the other elements within the circuitry.

Figure 10D:
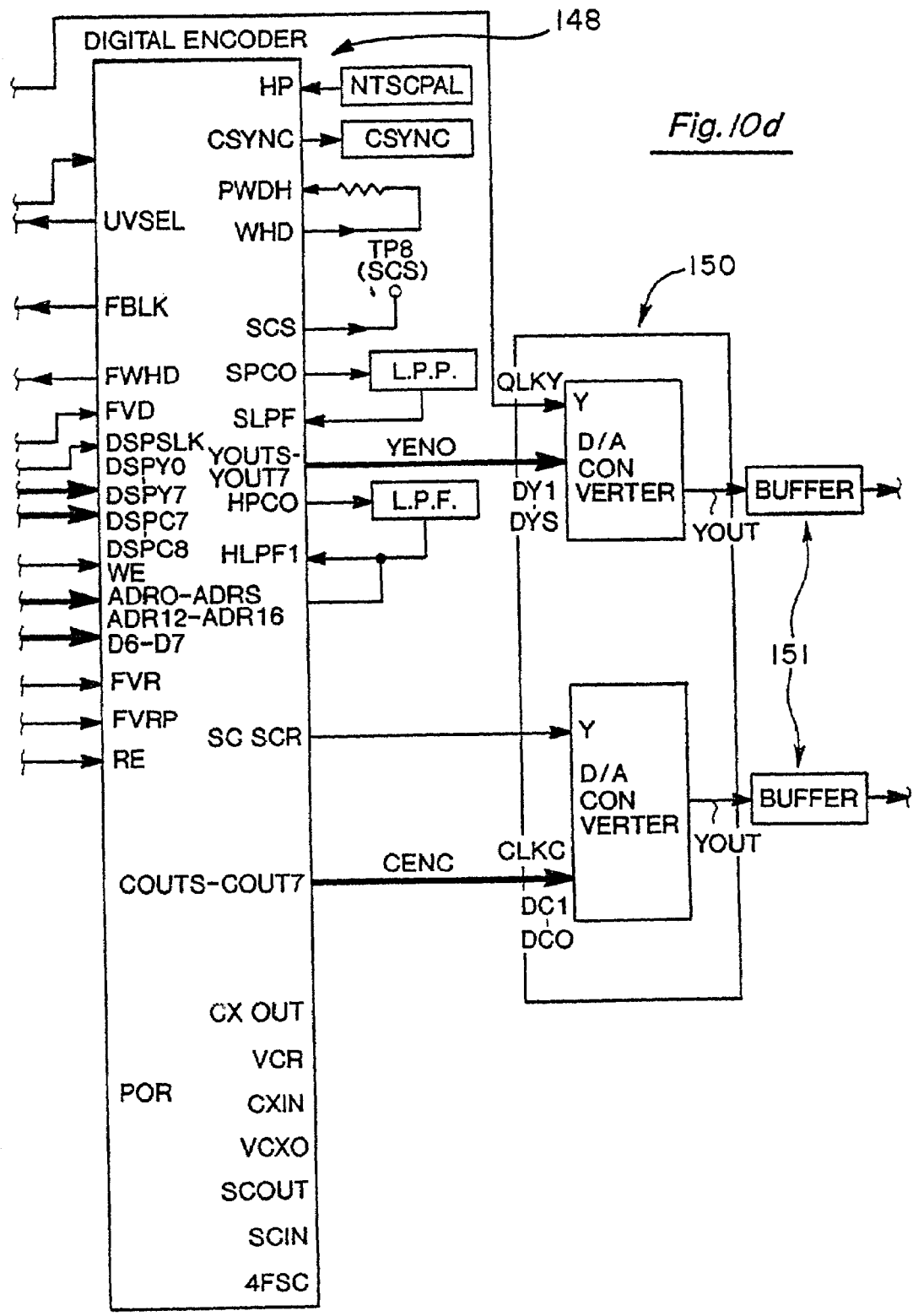

After the signal is processed by digital signal processor 144, the signal is sent to digital encoder 148 illustrated in FIG. 10d. Some of the more important functions of digital encoder 148 are to encode the digital signal with synchronization, modulated chroma, blanking, horizontal drive, and the other components necessary so that the signal may be placed in a condition for reception by a video device such as a television monitor. As also illustrated in FIG. 10d, once the signal has passed through digital encoder 148, the signal is reconverted into an analog signal through digital to analog converter 150.

Figure 10E:
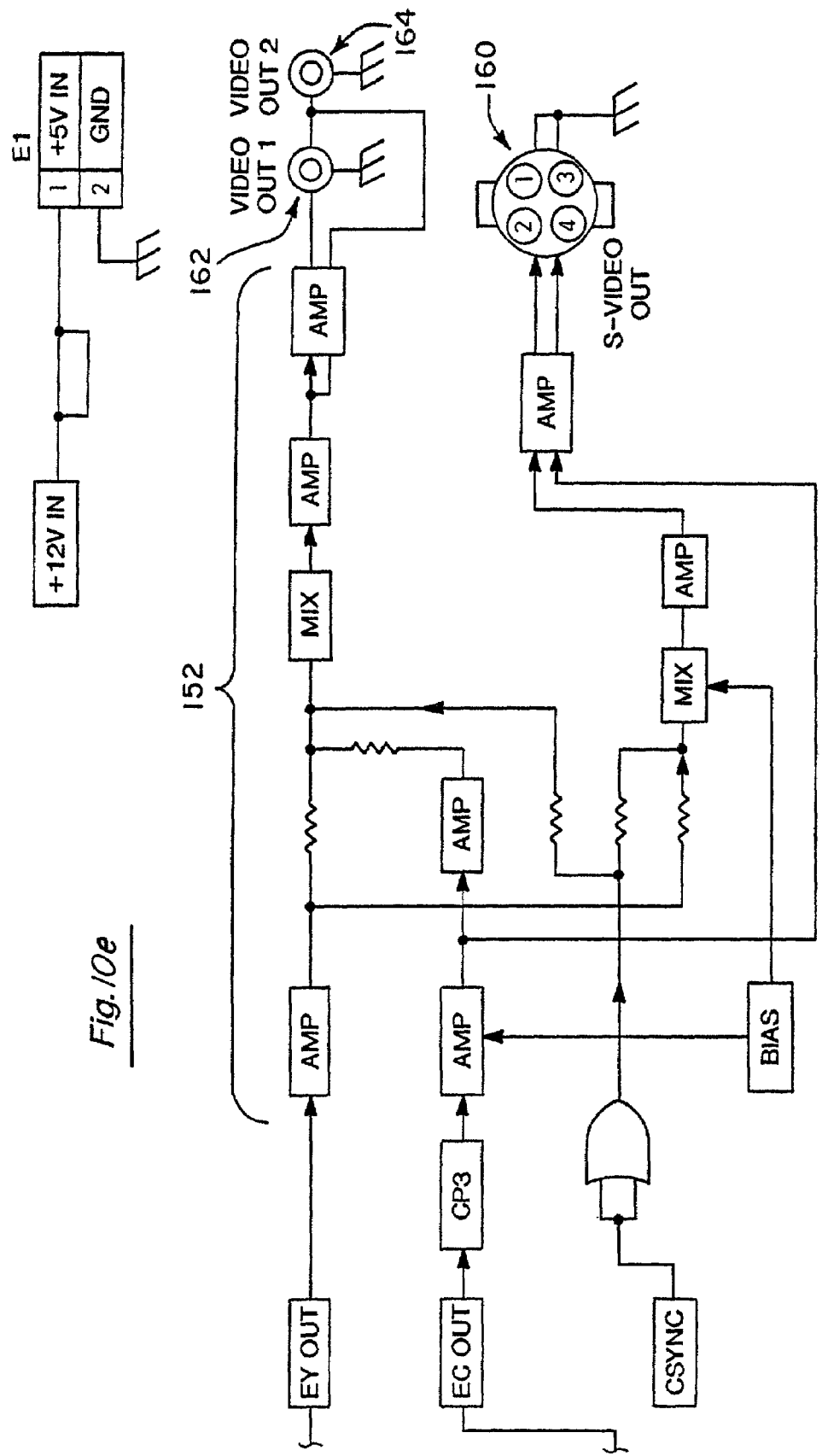

This reconverted analog signal is then buffered at buffers 151 and then sent to amplifier group 152 of FIG. 10e which amplifies the signal so that it is readily accepted by a desired video device. Specifically, as shown in FIG. 10e, one SVHS outlet is provided at 160, and two composite or NTSC outlets are provided at 162 and 164, respectively.

From the foregoing, it is apparent that an entire imaging device may be incorporated within the distal tip of the camera module, or may have some elements of the imaging device being placed in the housing of the communication device. Based upon the type of image sensor used, the profile area of the imaging device may be made small enough to be placed into a camera module which has a very small diameter.

This invention has been described in detail with reference to particular embodiments thereof, but it will be understood that various other modifications can be effected within the spirit and scope of this invention.

What is claimed is:

1. In a wireless telephone for conducting wireless telephonic communications, the improvement comprising:
   a video system integral with said telephone for receiving and transmitting video images, and for viewing said video images, said video system comprising;
   a camera module housing an image sensor therein, said image sensor including an array of pixels for receiving images thereon, said image sensor further including circuitry means on said first plane and coupled to said array of pixels for timing and control of said array of pixels, said image sensor producing a pre-video signal, a first circuit board mounted in said camera module adjacent said image sensor and electrically coupled to said image sensor, said first circuit board including circuitry means for converting said pre-video signal to a desired video format, said camera module further including a transceiver radio element mounted therein and electrically communicating with said first circuit board to transmit said converted pre-video signal;
   a transceiver radio module mounted in the wireless telephone for wirelessly communicating with said transceiver element in said camera module to receive said converted pre-video signal;
   a video monitor attached to said wireless phone for viewing said video images, said video monitor electrically coupled to said transceiver radio module for displaying video images processed by said first circuit board.

2. A device, as claimed in claim 1, wherein:
said pixels are CMOS pixels.

3. A device, as claimed in claim 1, wherein:
said transceiver radio element and said transceiver radio module communicate by a Bluetooth communications standard.

4. A device, as claimed in claim 1, wherein:
said transceiver radio element and said transceiver radio module communicate by an IEEE 802.15.3 communications standard.

5. In a wireless telephone for conducting wireless telephonic communications, the improvement comprising:
   a video system integral with said telephone for receiving and transmitting video images, and for viewing said video images, said video system comprising;

a camera module housing an image sensor therein, said image sensor including an array of pixels for receiving images thereon, said image sensor further including circuitry means on said first plane and coupled to said array of pixels for timing and control of said array of pixels, said image sensor producing a pre-video signal;

said camera module further including a transceiver radio element mounted therein and electrically communicating with said image sensor to transmit said pre-video signal;

a transceiver radio module mounted in the wireless telephone for wirelessly communicating with said radio transceiver element in said camera module to receive said pre-video signal;

a first circuit board mounted in said wireless telephone and electrically coupled to said transceiver radio module, said first circuit board including circuitry means for converting said pre-video signal to a desired video format;

a video monitor attached to said wireless phone for viewing said video images, said video monitor electrically coupled to said transceiver radio module for displaying video images processed by said first circuit board.

6. A device, as claimed in claim 5, wherein:
said pixels are CMOS pixels.

7. A device, as claimed in claim 5, wherein:
said transceiver radio element and said transceiver radio module communicate by a Bluetooth standard.

8. A device, as claimed in claim 5, wherein:
said transceiver radio element and said transceiver radio module communicate by an IEEE 802.15.3 standard.

9. In a video telephone for receiving and transmitting telephone communications to include video signals transmitted by the user of the phone, and video signals received from the party to whom a call was made, the video telephone including a housing, and a video monitor for viewing the video signals, the improvement comprising:

a camera module for taking video images, said camera module wirelessly communicating with circuitry within said video telephone enabling video signals to be transmitted from said camera module to said video telephone for viewing by said user or for further transmission to another party, said camera module including an image sensor housed therein, said image sensor lying in a first plane and including an array of pixels for receiving images thereon, said image sensor further including circuitry means on said first plane and coupled to said array of said pixels for timing and control of said array of pixels, said image sensor producing a pre-video signal, a first circuit board electrically connected to said image sensor and mounted within said camera module adjacent said image sensor, said first circuit board including circuitry means for converting said pre-video signal to a desired video format, and a transceiver radio element mounted in said camera module and electrically coupled to said first circuit board for transmitting said converted pre-video signal wirelessly to the video telephone.

10. A device, as claimed in claim 9, wherein:
said pixels are CMOS pixels.

11. A device, as claimed in claim 9, wherein:
said transceiver radio element communicates with the video telephone by a Bluetooth communications standard.

12. A device, as claimed in claim 9, wherein:
said transceiver radio element communicates with the video telephone by an IEEE 802.15.3 communications standard.

13. In a video telephone for receiving and transmitting telephone communications to include video signals transmitted by the user of the phone, and video signals received from the party to whom a call was made, the video telephone including a housing, and a video monitor for viewing the video signals, the improvement comprising:

a camera module for taking video images, said camera module wirelessly communicating with circuitry within said video telephone enabling video signals to be transmitted from said camera module to said video telephone for viewing by said user or for further transmission to another party, said camera module including an image sensor housed therein, said image sensor lying in a first plane and including an array of pixels for receiving images thereon, said image sensor further including circuitry means on said first plane and coupled to said array of said pixels for timing and control of said array of pixels, said image sensor producing a pre-video signal, and a transceiver radio element mounted in said camera module and electrically coupled to said image sensor board for transmitting the pre-video signal wirelessly to the video telephone, wherein the pre-video signal is further processed in the video telephone for viewing.

14. A device, as claimed in claim 13, wherein:
said pixels are CMOS pixels.

15. A device, as claimed in claim 13, wherein:
said transceiver radio element communicates with the video telephone by a Bluetooth communications standard.

16. A device, as claimed in claim 13, wherein:
said transceiver radio element communicates with the video telephone by an IEEE 802.15.3 communications standard.

17. A video telephone for conducting telephonic communications including receiving and transmitting video images between two parties of a telephone call, said video telephone comprising:

an image sensor lying in a first plane including an array of pixels for receiving images thereon, said image sensor further including circuitry means on said first plane and coupled to said array of pixels for timing and control of said array of pixels, said image sensor producing a pre-video signal;

a first circuit board electrically communicating with said image sensor, said first circuit board including circuitry means for converting said pre-video signal to a desired video format;

a camera module housing said image sensor and said first circuit board;

a transceiver radio element mounted in said camera module and communicating with said first circuit board for wirelessly transmitting the converted pre-video signal;

a transceiver radio module communicating wirelessly with said transceiver radio element for receiving the converted pre-video signal;

a transceiver/amplifier section electrically coupled to said transceiver radio module for amplifying and further transmitting the converted pre-video signal, and for receiving and amplifying video and audio signals transmitted by the other party of the telephone call;

a digital signal processor electrically coupled to said transceiver radio module and said transceiver/amplifier section, said digital signal processor further conditioning said converted pre-video signal prior to said converted pre-video signal being manipulated by said transceiver/amplifier section, and also for conditioning video and audio signals received by said transceiver/amplifier section from the other party of the telephone call;

a microphone electrically communicating with said digital signal processor for receiving sound and converting the sound to audio signals;

a speaker electrically communicating with said digital signal processor for broadcasting audio signals;

a video monitor attached to said video phone, said video monitor for selectively displaying the converted pre-video signals, and for selectively displaying video images received by said transceiver/amplifier section from the other party of the telephone call;

a video switch communicating with said transceiver radio module and said digital signal processor for switching video images to be viewed on said video monitor, a user being able to selectively display video images from the converted pre-video signal or video images received by the transceiver/amplifier section from the other party of the telephone call; and a power supply mounted to said video telephone for providing power thereto.

18. A device, as claimed in claim 17, wherein:
said pixels are CMOS pixels.

19. A device, as claimed in claim 17, wherein:
said transceiver radio element communicates with the video telephone by a Bluetooth communications standard.

20. A device, as claimed in claim 17, wherein:
said transceiver radio element communicates with the video telephone by an IEEE 802.15.3 communications standard.

21. A video telephone for conducting telephonic communications including receiving and transmitting video images between two parties of a telephone call, said video telephone comprising:

an image sensor lying in a first plane, and an array of pixels for receiving images thereon, said image sensor further including circuitry means on said first plane and coupled to said array of pixels for timing and control of said array of pixels, said image sensor producing a pre-video signal;

a camera module housing said image sensor therein;

a transceiver radio element mounted in said camera module and communicating with said image sensor for wirelessly transmitting the pre-video signal;

a transceiver radio module communicating wirelessly with said transceiver radio element for receiving the pre-video signal;

a first circuit board electrically communicating with said transceiver radio module, said first circuit board including circuitry means for converting said pre-video signal to a desired video format;

a transceiver/amplifier section electrically coupled to said first circuit board for amplifying and further transmitting the converted pre-video signal, and for receiving and amplifying video and audio signals transmitted by the other party of the telephone call;

a digital signal processor electrically coupled to said first circuit board and said transceiver/amplifier section, said digital signal processor further conditioning said converted pre-video signal prior to said converted pre-video signal being manipulated by said transceiver/amplifier section, and also for conditioning the video and audio signals received by said transceiver/amplifier section from the other party of the telephone call;

a microphone electrically communicating with said digital signal processor for receiving sound and converting the sound to audio signals;

a speaker electrically communicating with said digital signal processor for broadcasting audio signals;

a video monitor attached to said video phone, said video monitor for selectively displaying the converted pre-video signals, and for selectively displaying video images received by said transceiver/amplifier section from the other party of the telephone call;

a video switch communicating with said transceiver radio module and said digital signal processor for switching video images to be viewed on said video monitor, a user being able to selectively display video images from the converted pre-video signal or video images received by the transceiver/amplifier section from the other party of the telephone call; and a power supply mounted to said video telephone for providing power thereto.

22. A device, as claimed in claim 21, wherein:
said pixels are CMOS pixels.

23. A device, as claimed in claim 21, wherein:
said transceiver radio element communicates with the video telephone by a Bluetooth communications standard.

24. A device, as claimed in claim 21, wherein:
said transceiver radio element communicates with the video telephone by an IEEE 802.15.3 communications standard.

25. In a wireless telephone for conducting wireless telephonic communications, the improvement comprising:

a video system integral with said telephone for receiving and transmitting video images, and for viewing said images, said video system comprising:

a camera module housing an image sensor therein, said image sensor lying in a first plane and including an array of pixels for receiving images thereon, circuitry means electrically coupled to said array of pixels for timing and control of said array of pixels, said circuitry means for timing and control being placed remote from said array of pixels on a second plane, said image sensor producing a pre-video signal, a first circuit board lying in a third plane and electrically coupled to said image sensor, said first circuit board including circuitry means for processing and converting said pre-video signal to a desired video format, a transceiver radio element communicating with said first circuit board for transmitting said converted pre-video signal;

a transceiver radio module mounted in said telephone for wirelessly receiving said converted pre-video signal; and a video monitor attached to said wireless phone for viewing said video images, said video monitor communicating with said transceiver radio module, and displaying video images processed by said first circuit board.

26. A device, as claimed in claim 25, wherein:
said pixels are CMOS pixels.

27. A device, as claimed in claim 25, wherein:
said transceiver radio element communicates with the video telephone by a Bluetooth communications standard.

28. A device, as claimed in claim 25, wherein:
said transceiver radio element communicates with the video telephone by an IEEE 802.15.3 communications standard.

29. In a video telephone for receiving and transmitting telephone communications to include video signals transmitted by the user of the phone, and video signals received from the party to whom a call is made, the video telephone including a video monitor for viewing the video signals, the improvement comprising:
a camera module for taking video images, said camera module communicating with circuitry within said video telephone enabling video signals to be transmitted from said camera module to said video telephone for viewing by said user or for further transmission to another party, said camera module including an image sensor housed therein, said image sensor lying in a first plane and including an array of pixels for receiving images thereon, said image sensor producing a pre-video signal, a first circuit board mounted adjacent said image sensor and electrically connected to said image sensor, said first circuit board including circuitry means for timing and control of said array of pixels and circuitry means for processing and converting said pre-video signal to a desired video format, and a transceiver radio element communicating with said first circuit board for wirelessly transmitting said converted pre-video signal.

30. A device, as claimed in claim 29, wherein:
said pixels are CMOS pixels.

31. A device, as claimed in claim 29, wherein:
said transceiver radio element transmits by a Bluetooth communications standard.

32. A device, as claimed in claim 29, wherein:
said transceiver radio element transmits by an IEEE 802.15.3 communications standard.

33. In a video telephone for receiving and transmitting telephone communications to include video signals transmitted by the user of the phone, and video signals received from the party to whom a call is made, the video telephone including a video monitor for viewing the video signals, the improvement comprising:
a camera module for taking video images, said camera module communicating with circuitry within said video enabling video signals to be transmitted from said camera module to said video telephone for viewing by said user or for further transmission to another party, said camera module including an image sensor housed therein and lying in a first plane, said image sensor including an array of pixels for receiving images thereon, said image sensor producing a pre-video signal, and a transceiver radio element communicating with said image sensor for wirelessly transmitting said pre-video signal.

34. A device, as claimed in claim 33, wherein:
said pixels are CMOS pixels.

35. A device, as claimed in claim 33, wherein:
said transceiver radio element transmits by a Bluetooth communications standard.

36. A device, as claimed in claim 33, wherein:
said transceiver radio element transmits by an IEEE 802.15.3 communications standard.

37. In a video telephone for receiving and transmitting telephone communications to include video signals transmitted by the user of the phone, and video signals received from the party to whom a call was made, the video telephone including a video monitor for viewing the video signals, the improvement comprising:
a camera module for taking video images, said camera module communicating with circuitry within said video enabling video signals to be transmitted from said camera module to said video telephone for viewing by said user or for further transmission to another party, said camera module including an image sensor housed therein, said image sensor lying in a first plane and including an array of pixels for receiving images thereon, said image sensor further including circuitry means electrically coupled to said array of said pixels for timing and control of said array of pixels, said circuitry means for timing and control placed remote from said array of pixels on a second plane, said image sensor producing a pre-video signal, a first circuit board electrically connected to said image sensor and lying in a third plane, said first circuit board including circuitry means for processing and converting said pre-video signal to a desired video format, and a radio transceiver element communicating with said first circuit board for wirelessly transmitting said converted pre-video signal.

38. A device, as claimed in claim 37, wherein:
said pixels are CMOS pixels.

39. A device, as claimed in claim 37, wherein:
said transceiver radio element transmits by a Bluetooth communications standard.

40. A device, as claimed in claim 37, wherein:
said transceiver radio element transmits by an IEEE 802.15.3 communications standard.

41. In a video telephone for receiving and transmitting telephone communications to include video signals transmitted by the user of the phone, and video signals received from the party to whom a call was made, the video telephone including a video monitor for viewing the video signals, the improvement comprising:
a camera module for taking video images, said camera module communicating with circuitry within said video telephone enabling viewing of said video images on said video telephone and enabling video signals to be transmitted from said camera module for viewing by said party, said camera module including an image sensor housed therein, said image sensor lying in a first plane and including an array of pixels for receiving images thereon, said image sensor further including circuitry means electrically coupled to said array of said pixels for timing and control of said array of pixels, said circuitry means for timing and control placed remote from said array of pixels on a second plane, said image sensor producing a pre-video signal, and a radio transceiver element communicating with said image sensor for wirelessly transmitting said pre-video signal.

42. A device, as claimed in claim 41, wherein:
said pixels are CMOS pixels.

43. A device, as claimed in claim 41, wherein:
said transceiver radio element transmits by a Bluetooth communications standard.

44. A device, as claimed in claim 41, wherein:
said transceiver radio element transmits by an IEEE 802.15.3 communications standard.

45. A video telephone for conducting telephonic communications including receiving and transmitting video images between two parties of a telephone call, said video telephone comprising:

an image sensor lying in a first plane including an array of pixels for receiving images thereon, said image sensor producing a pre-video signal;

a first circuit board electrically communicating with said image sensor, said first circuit board including circuitry means for timing and control of said array of pixels and circuitry means for processing and converting said pre-video signal to a desired video format;

a transceiver radio element communicating with said first circuit board for wirelessly transmitting said converted pre-video signal;

a camera module housing said image sensor, said first circuit board, and said transceiver radio element therein;

a transceiver radio module mounted in said telephone for receiving said converted pre-video signal;

a transceiver/amplifier section electrically coupled to said transceiver radio module for amplifying and further transmitting the converted pre-video signal, and for receiving and amplifying video and audio signals transmitted by the other party of the telephone call;

a digital signal processor electrically coupled to said transceiver radio module and said transceiver/amplifier section, said digital signal processor further conditioning said pre-video signal which is first conditioned by said first circuit board, and also for conditioning video and audio signals received by said transceiver/amplifier section from the other party of the telephone call;

a microphone electrically communicating with said digital signal processor for receiving sound and converting the sound to audio signals;

a speaker electrically communicating with said digital signal processor for broadcasting audio signals;

a video monitor attached to said video phone, said video monitor for selectively displaying images from said imaging device, and for selectively displaying video images received by said transceiver/amplifier section;

a video switch communicating with said first circuit board and said digital signal processor for switching video images to be viewed on said video monitor; and a power supply mounted to said video telephone for providing power thereto.

46. A device, as claimed in claim 45, wherein:
said pixels are CMOS pixels.

47. A device, as claimed in claim 45, wherein:
said transceiver radio element transmits by a Bluetooth communications standard.

48. A device, as claimed in claim 45, wherein:
said transceiver radio element transmits by an IEEE 802.15.3 communications standard.

49. A video telephone for conducting telephonic communications including receiving and transmitting video images between two parties of a telephone call, said video telephone comprising:

an image sensor lying in a first plane including an array of pixels for receiving images thereon, said image sensor producing a pre-video signal;

a first circuit board electrically communicating with said image sensor, said first circuit board including circuitry means for timing and control of said array of pixels;

a transceiver radio element communicating with said first circuit board for wirelessly transmitting said pre-video signal;

a camera module housing said image sensor, said first circuit board, and said transceiver radio element therein;

a transceiver radio module mounted in said telephone for receiving said pre-video signal;

a second circuit board electronically communicating with said transceiver radio module, said second circuit board including circuitry means for converting said pre-video signal to a desired video format;

a transceiver/amplifier section electrically coupled to said second circuit board for amplifying and further transmitting said converted pre-video signal, and for receiving and amplifying video and audio signals transmitted by the other party of the telephone call;

a digital signal processor electrically coupled to said second circuit board and said transceiver/amplifier section, said digital signal processor further conditioning said converted pre-video signal which is first conditioned by said second circuit board, and also for conditioning video and audio signals received by said transceiver/amplifier section from the other party of the telephone call;

a microphone electrically communicating with said digital signal processor for receiving sound and converting the sound to audio signals;

a speaker electrically communicating with said digital signal processor for broadcasting audio signals;

a video monitor attached to said video phone, said video monitor for selectively displaying images from said imaging device, and for selectively displaying video images received by said transceiver/amplifier section from the other party of the telephone call;

a video switch communicating with said second circuit board and said digital signal processor for switching video images to be viewed on said video monitor, a user being able to selectively display video images from the imaging device or video images received by the transceiver/amplifier section from the other party of the telephone call; and a power supply mounted to said video telephone for providing power thereto.

50. A device, as claimed in claim 49, wherein:
said pixels are CMOS pixels.

51. A device, as claimed in claim 49, wherein:
said transceiver radio element transmits by a Bluetooth communications standard.

52. A device, as claimed in claim 49, wherein:
said transceiver radio element transmits by an IEEE 802.15.3 communications standard.

53. A video telephone for conducting telephonic communications including receiving and transmitting video images between two parties of a telephone call, said video telephone comprising:

an image sensor lying in a first plane, and an array of pixels for receiving images thereon, said image sensor further including circuitry means electrically coupled to said array of pixels for timing and control of said array of pixels, said circuitry means for timing and control being placed remote from said array of pixels on a second plane, said image sensor producing a pre-video signal;

a first circuit board electrically coupled with said image sensor and lying in a third plane, said first circuit board including circuitry means for processing and converting said pre-video signal to a desired video format;

a transceiver radio element communicating with said first circuit board to wirelessly transmit the converted pre-video signal;

a camera module housing said image sensor, said first circuit board and said transceiver radio element;

a transceiver radio module mounted in said videophone for wirelessly receiving said converted pre-video signal, a transceiver/amplifier section electrically coupled to said transceiver radio module for amplifying and further transmitting said converted pre-video signal and for receiving and amplifying video and audio signals transmitted by the other party of the telephone call;

a digital signal processor electrically coupled to said transceiver radio module and said transceiver/amplifier section, said digital signal processor further conditioning said converted pre-video signal which is first conditioned by said first circuit board, and also for conditioning video and audio signals received by said transceiver/amplifier section from the other party of the telephone call;

a microphone electrically communicating with said digital signal processor for receiving sound and converting the sound to audio signals;

a speaker electrically communicating with said digital signal processor for broadcasting audio signals;

a video monitor attached to said video phone, said video monitor for selectively displaying images from said imaging device, and for selectively displaying video images received by said transceiver/amplifier section from the other party of the telephone call;

a video switch communicating with said transceiver radio module and said digital signal processor for switching video images to be viewed on said video monitor, a user being able to selectively display video images from the imaging device or video images received by the transceiver/amplifier section from the other party of the telephone call; and a power supply mounted to said video telephone for providing power thereto.

54. A device, as claimed in claim 53, wherein:
said pixels are CMOS pixels.

55. A device, as claimed in claim 53, wherein:
said transceiver radio element transmits by a Bluetooth communications standard.

56. A device, as claimed in claim 53, wherein:
said transceiver radio element transmits by an IEEE 802.15.3 communications standard.

57. In a method for conducting video telephone communications with a video telephone, the improvement comprising the steps of:

providing a camera module having an image sensor housed therein;

removing the camera module from connection with the video telephone;

pointing the camera module at a targeted object and selectively taking video images of the targeted object;

wirelessly transmitting the video images taken by the image sensor to the video telephone;

processing the video images transmitted by the camera module; and selectively viewing the video images on the video telephone and selectively transmitting the video images to another party.

58. A method, as claimed in claim 57, wherein:
said image sensor includes a CMOS pixel array.

59. In a wireless telephone for conducting wireless telephonic communications, the improvement comprising:

a camera module housing an image sensor therein, said camera module for producing video images of a targeted object;

means for wirelessly interconnecting said camera module to said wireless telephone, said means for wirelessly interconnecting enabling said camera module to be selectively displaced away from and not in contact with said wireless telephone; and a video monitor attached to said wireless phone for selectively viewing video images taken by said camera module, and for selectively viewing incoming video images transmitted by another party.

60. A device, as claimed in claim 59, wherein:
said video telephone includes a housing, and an opening in said housing for receiving said camera module so as to place said camera module in a stored position.

61. In a video telephone for conducting communications including receiving and transmitting video images between two parties of a video telephone call, the improvement comprising:

a camera module housing an image sensor therein;

a camera module battery housed within said camera module for providing power to said camera module;

a camera battery charge circuit housed within the video telephone;

a telephone battery housed within the telephone for providing power to said camera battery charge circuit; and wherein the camera module is received in the video telephone so said camera module battery electrically communicates with said camera battery charge circuit to selectively charge said camera module battery.

62. A method of powering and recharging a camera module for use with a video telephone, said method comprising the steps of:

providing a video telephone including a camera battery charge circuit and a telephone battery housed therein;

providing a camera module housing an image sensor therein for taking video images, and a camera module battery housed within said camera module for selectively powering said camera module;

removing said camera module from seated engagement with the video telephone resulting in activation of said camera module battery for powering said camera module; and returning said camera module to its seated position with said video telephone and in electrical communication with the battery charge circuit to charge said camera module battery.

* * * * *